United States Patent
Meddings et al.

(10) Patent No.: US 12,336,809 B2
(45) Date of Patent: Jun. 24, 2025

(54) CONTACTLESS PATIENT MOTION MONITORING

(71) Applicant: THE REGENTS OF THE UNIVERSITY OF MICHIGAN, Ann Arbor, MI (US)

(72) Inventors: Jennifer Meddings, Ann Arbor, MI (US); James A. Ashton-Miller, Ann Arbor, MI (US); Shiyu Wang, Seattle, WA (US); Jessica Marie Ameling, Ann Arbor, MI (US); Shuai Xiong, Shanghai City (CN); Zizheng Zhang, Fort Lee, NJ (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 662 days.

(21) Appl. No.: 17/630,367

(22) PCT Filed: Jul. 24, 2020

(86) PCT No.: PCT/US2020/043428
§ 371 (c)(1),
(2) Date: Jan. 26, 2022

(87) PCT Pub. No.: WO2021/021609
PCT Pub. Date: Feb. 4, 2021

(65) Prior Publication Data
US 2022/0322971 A1    Oct. 13, 2022

Related U.S. Application Data

(60) Provisional application No. 62/879,021, filed on Jul. 26, 2019.

(51) Int. Cl.
*A61B 5/11* (2006.01)
*A61B 5/00* (2006.01)

(52) U.S. Cl.
CPC .......... *A61B 5/1114* (2013.01); *A61B 5/1115* (2013.01); *A61B 5/1116* (2013.01);
(Continued)

(58) Field of Classification Search
CPC .... A61B 5/1115; A61B 5/6892; A61B 5/6894
See application file for complete search history.

(56) References Cited

U.S. PATENT DOCUMENTS 3,325,799 A    6/1967 Farris
7,253,366 B2    8/2007 Bhai
(Continued)

FOREIGN PATENT DOCUMENTS

CN    204306471 U    5/2015
CN    107 198 516 A    9/2017
(Continued)

OTHER PUBLICATIONS

Stepanov et al., "Performance Criteria for the Identification of Inertial Sensor Error Models", 2019 (Year: 2019).*
(Continued)

*Primary Examiner* — Eric F Winakur
*Assistant Examiner* — Noah M Healy
(74) *Attorney, Agent, or Firm* — MARSHALL, GERSTEIN & BORUN LLP

(57) ABSTRACT

A system for real-time monitoring of movement of a person on a mattress includes sensor devices positioned on one or more peripheral surfaces of the mattress and configured to sense lateral accelerations of the peripheral surface(s). The sensor devices includes at least first and second sensor devices positioned on a first side surface of the mattress. A processing subsystem is configured to receive signals indicative of the sensed lateral accelerations of the peripheral surface(s) from the sensor devices, determine whether the sensed lateral accelerations correspond to one or more alert
(Continued)

conditions, and selectively cause, or not cause, one or more visual and/or audio indicators to be generated based on whether at least the sensed lateral accelerations correspond to the alert condition(s).

22 Claims, 13 Drawing Sheets

(52) U.S. Cl.
 CPC .......... *A61B 5/4094* (2013.01); *A61B 5/6892* (2013.01); *A61B 5/7405* (2013.01); *A61B 5/742* (2013.01); *A61B 5/746* (2013.01); *A61B 2562/0219* (2013.01)

(56) References Cited

U.S. PATENT DOCUMENTS

| | | | |
|---|---|---|---|
| 2007/0008156 | A1 | 1/2007 | Ueda et al. |
| 2007/0156031 | A1* | 7/2007 | Sullivan ............... A61B 5/7282 600/300 |
| 2013/0090571 | A1 | 4/2013 | Nourani et al. |
| 2013/0301897 | A1 | 11/2013 | Zhu et al. |
| 2014/0046184 | A1 | 2/2014 | Heinrich et al. |
| 2014/0371635 | A1 | 12/2014 | Shinar et al. |
| 2015/0015399 | A1 | 1/2015 | Gleckler et al. |
| 2015/0175111 | A1* | 6/2015 | Muramatsu ....... B60R 21/01516 702/150 |
| 2018/0008168 | A1* | 1/2018 | Pearlman ............... A61B 5/002 |
| 2019/0029547 | A1 | 1/2019 | Watarai et al. |
| 2019/0201271 | A1* | 7/2019 | Grey .................... A61B 5/6892 |
| 2020/0238854 | A1* | 7/2020 | Gandhi .................... B60N 2/99 |

FOREIGN PATENT DOCUMENTS

| | | | |
|---|---|---|---|
| EP | 3245943 | * | 11/2017 |
| EP | 3245943 | A1 | 11/2017 |
| EP | 3323342 | A1 | 5/2018 |
| JP | 2020081667 | * | 11/2018 |
| JP | 2020-081667 | A | 6/2020 |

OTHER PUBLICATIONS

International Search Report and Written Opinion for Application No. PCT/US/2020/043428, dated Oct. 5, 2020.
Baec, S. et al., "Implementation of Movement Detection System for Patient on Bed", Journal of Advanced Navigation Technology, Published on Oct. 30, 2015.
Chica, M. et al., "Real-time recognition of patient intentions from sequences of pressure maps using artificial neural networks", Computers in Biology and Medicine 42.4 (2012): 364-375.
Chung, P. et al., "Fabric-based pressure Sensor Array for Decubitus Ulcer Monitoring", Conference proceedings: . . . Annual International Conference of the IEEE Engineering in Medicine and Biology Society. IEEE Engineering in Medicine and Biology Society. Annual Conference vol. 2013 (2013).
Fulton, S. et al., "Prospective Study of 2 Bed Alarms for Detection of Nocturnal Seizures", Journal of Child Neurology, 28(11) (2012), 1430-1433.
Kutilek, P. et al., "Identification of Patient's Physiological Movements on the Bed by Strain Gauge Sensors Detect Torsion of the Elements of the Bed", MECHATRONIKA, 15th International Symposium, IEEE (2012).
Maki, H. et al., "A System for Monitoring Cardiac Vibration, Respiration, and Body Movement in Bed Using an Infrared", Engineering in Medicine and Biology Society (EMBC), 2010 Annual International Conference of the IEEE, IEEE (2010).
Patel, S. et al., "A review of wearable sensors and systems with application in rehabilitation." Journal of Neuroengineering and Rehabilitation 9.1 (2012): 21.
Senthilkumar, S. et al., "Design and study of ultrasound based automatic patient movement monitoring device for quantifying the intrafraction motion during teletherapy treatment", Journal of Applied Clinical Medical Physics 13.6 (Nov. 6, 2012): 82-90.
Spillman, Jr., W. B. et al., "A 'smart'bed for non-intrusive monitoring of patient physiological factors", Measurement Science and Technology 15.8 (Feb. 24, 2004): 1614.
Swisher, S. et al., "Impedance sensing device enables early detection of pressure ulcers in vivo", Nature Communications 2015, vol. 6, Article No. 6575 (Mar. 17, 2015).
Van Poppel K. et al., "Prospective Study of the Emfit Movement Monitor", Journal of Child Neurology, 2013;28(11):1434-1436.
Wang, H. et al. "Monitoring and Analysis of Sleep Pattern for People with Early Dementia", 2010 IEEE International Conference on Bioinformatics and Biomedicine Workshops (BIBMW), Hong, Kong, 2010, pp. 405-410.
Varshney, P. K., "Multisensor Data Fusion", Electronics & Communication Engineering Journal, Published in Dec. 1997.
Chung, P. et al., "Fabric-based Pressure Sensor Array for Decubitus Ulcer Monitoring", National Library of Medicine, Published Oct. 15, 2015, Retrieved from the Internet at: <https://pmc.ncbi.nlm.nih.gov/articles/PMC4606918/> (Apr. 21, 2025).
Wellsense, The M.A.P. System User Guide, Retrieved from the Internet at <https://myagilitiimg.agilitihealth.com/userGuides/prod2455_MAPSYS.pdf> (Apr. 21, 2025).
Smith & Nephew, LEAF Patient Monitoring System, Retrieved from the Internet at <https://www.sn-leaf.com/how-it-works> (Apr. 21, 2025).
HiPass Design LLC, SAMi the Sleep Activity Monitor, Retrieved from the Internet at <https://www.samialert.com> (Apr. 21, 2025).
Rondish, Fall Management, Retrieved from the Internet at: < http://www.rondish.com/fall-management> (Apr. 21, 2025).
SensaRx, LLC., SafeWander, Retrieved from the Internet at <https://www.safewander.com> (Apr. 21, 2025).
Respiratory Therapy, "EarlySense Home Monitoring Predicts Hospital Readmissions for HF", Feb. 25, 2016, Retrieved from the Internet at: <https://www.respiratory-therapy.com/department-management/clinical/earlysense-home-monitoring-predicts-hospital- readmissions-hf/> (Apr. 21, 2025).
Medline Industries, Inc., Sensable Care System Catalog, Retrieved from the Internet at: <https://www.medline.com/media/catalog/Docs/MKT/LITe17183_SSH_Sensable_Care_1786035.pdf> (Apr. 21, 2025).
Yang, S., "Smart bandage' detects bedsores before they are visible to doctors", UC Berkeley News, Published Mar. 17, 2015, Retrieved from the Internet at: <https://news.berkeley.edu/2015/03/17/smart-bandages-detect-bedsores/> (Apr. 21, 2025).

* cited by examiner

1000

| motion | shoulder | hip | heels |
|---|---|---|---|
| still | ↑ | ↑ | ↑ |
| left roll | ↓ | ↓ | ↓ |
| right roll | ↓ | ↓ | ↓ |
| small feet movement | ↑ | ↑ | ↓ |
| large feet movement | ↑ | ↓ | ↓ |
| bed exit | — | — | — |
| clonic seizure | — | — | — |

*FIG. 10*

CONTACTLESS PATIENT MOTION MONITORING

GOVERNMENT LICENSE RIGHTS

This invention was made with government support under P30 HS024385 awarded by the Agency for Healthcare Research and Quality. The government has certain rights in the invention.

TECHNICAL FIELD

The present application relates generally to patient care, and more specifically to a system and method that can detect clinically important motions of a person on a bed, chair, or other supporting structure.

BACKGROUND

Patient motions are important signs of vital status (i.e., one of the "vitals" in patient monitoring). Patient movement is typically examined and documented primarily via direct observation by nurses or physicians at the bedside, with no monitoring system when the caregivers are away (e.g., outside a hospital room). The lack of direct observation means that various types of patient hazards can go undetected for a significant period of time, causing patients to miss out on medical care when it is most needed.

For example, caregivers may be unable to detect, in a timely manner, inadequate self-movement in bed, which can lead to skin breakdown known as "pressure ulcers" (also called pressure injuries, decubitus ulcers, or bed sores). Pressure ulcers can rapidly develop in frail or critically ill patients who do not shift their body position enough while in bed. These lesions are often caused by sustained, localized, high pressure from the support surface of the bed, which occludes blood flow in the skin (typically over a bony prominence) and can lead to local inflammation, breakdown, and infection of healthy skin. Examples of skin areas that are especially at risk include those overlying the sacrum, heels, elbows, or occiput, where there is typically little fat or muscle overlying the bone. While peripheral nerves in the affected skin and tissues normally transmit warning signals to the brain when the level of localized discomfort reaches a threshold, nerve transmission can be blocked if a peripheral nerve suffers compression by an external pressure of about 80 mm Hg or more for two hours, thereby precluding the ability of the nerve to transmit the necessary warning signals to the brain. Thus, time is of the essence in identifying when a patient is not moving enough to protect his or her own skin. In particular, caregivers must be aware of the lack of movement in order to implement skin protection plans that prevent pressure ulcers from forming. For example, caregivers may help the patient to reposition in bed to avoid prolonged pressure on certain areas of the skin. The risk of pressure ulcers increases for those patients who are too ill to adequately move their bodies. Because insurers are reluctant to reimburse for the treatment of decubitus ulcers, health care systems are increasingly motivated to prevent their occurrence in the first place. It has been reported that the prevalence of pressure ulcers in the United States alone affects an estimated 1.5 to 3 million people annually.

As another example, caregivers may be unable to detect, in a timely manner, unexpected movement out of bed by patients who have a high risk of falling when moving without assistance, leading to head injuries, fractures, etc. Falls and fall-related injuries that occur when weak or disoriented patients unexpectedly get up from bed in hospitals or nursing homes are a major problem for patients, care providers, and insurers. Moreover, undetected bed egress by a patient can cause the various IVs, leads, cables, etc., attached to the patient to be inadvertently pulled out.

As yet another example, caregivers may be unable to detect, in a timely manner, repetitive or otherwise abnormal physical movements that could be indicative of seizure activity (e.g., clonic seizure in epilepsy patients) and might be fatal if not detected early. A sudden seizure can happen at any time, and can cause bruises, cuts or burns because of large, uncontrolled movements. More seriously, an episode with a generalized seizure, long seizure, or seizure with fall could lead to broken bones, concussions or breathing problems. Rarely, in about one out of every 1,000 epilepsy patients, sudden unexpected death in epilepsy, or "SUDEP," can occur. Early caregiver interaction can alleviate or prevent each of these adverse consequences.

To address some of the issues above, a variety of patient monitoring devices and techniques for detecting in-bed patient motion have been proposed. Some solutions employ a wearable device that contacts the patient's skin or clothes (see, e.g., EP 3323342A1). These wearable devices may have embedded inertial measurement units (IMUs), such as accelerometers, rate gyroscopes, magnetometers, or a combination thereof, to measure the motion characteristics of patients. The outputs of such a device can be used to estimate the status of a patient's medical conditions, and to determine whether a notification should be sent to a caregiver. Some patients find these wearable devices uncomfortable, however, due to localized skin pressure and/or constraints imposed on the patient's free movement (e.g., due to leads used to power the devices), particularly in view of the fact that many patients are already tethered to other equipment (e.g., via electrocardiogram leads, heart rate and blood pressure leads, catheters and intravenous (IV) tubes, etc.). While wireless wearable sensors have also been proposed, the embedded batteries and wireless communication modules pose a risk of battery overheating and burns (for lithium ion batteries), and the electromagnetic hazards are significant. Moreover, the battery has limited power capacity, and needs to be recharged regularly. Recharging of such devices is inconvenient for caregivers, who typically have many other duties (e.g., on a busy ward).

Other solutions utilize a "smart" mat or pad beneath the patient (see, e.g., US 2007/0008156A1 and US 2013/0090571A1). However, these sensors cannot be made from cotton or other soft, absorbent materials that are favored by clinicians where sustained skin contact is likely. Instead, such mats/pads are made of plastics that are impermeable to moisture, and therefore alter the temperature and humidity of the air surrounding the patient's skin. This can cause moisture build-up in the skin (from sweat), thereby increasing the friction force between the skin and mat/pad and significantly increasing the risk of pressure ulcers. Moreover, urine or feces from the patient can cause shorting of the electrical conductors in the pressure mat/pad, increasing the risk of electrical shock. Finally, with increasing obesity, the gravitational and inertial forces exerted by a patient on localized areas of the pressure mat/pad can cause early breakdown of the mat/pad due to fatigue of the conductors, wires, or leads within the mat/pad.

Still other solutions seek to avoid some of the above-noted problems by using sensors that do not contact the patient (see, e.g., EP 3245943A1, US 2013/0301897A1, and US 2014/0046184A1). A variety of contactless systems have been proposed, including systems that use ultrasound sensors, x-rays, infrared diodes, cone beam computed tomography (CBCT) images, or other technologies. These solutions, however, typically need to be placed next to the patient's bed (e.g., on a pole). This can cause a substantial increase in the effective dimensions of the hospital bed, which cannot easily be tolerated in hospital settings that have numerous monitoring devices around the hospital bed. Moreover, prominent structures can serve as a barrier for doctors, nurses, or other caregivers who need to inspect the patient. For example, the caregivers may need to remove sensor poles and/or other structures before the inspection, and then return the structures back to their place after the inspection.

Yet another proposed solution places motion sensors on the bed frame, inside the bed mattress, or between two mattresses (see, e.g., U.S. Pat. No. 7,253,366B2 and CN 204306471 U). These monitoring devices modify the intrinsic structure of the hospital bed in a manner that must be addressed at the time of manufacture. The redesign of existing beds can give rise to substantial costs that are typically passed on to consumers. Moreover, the sheer variety of hospital bed designs can make it difficult to embed the sensors in all beds. For example, some mattresses have spring coils while others are inflated. While one proposed device would place the sensor pads under the bed wheels or legs, this approach sacrifices specificity of movement detection. For example, placing a sensor pad under each of the three or four wheels or legs of a hospital bed may allow detection of a completed bed exit, but would make it difficult or impossible to detect the specific body movements that lead up to bed exit.

While other proposed solutions place a sensor on the side of a mattress, these approaches, too, have been unable to distinguish different, relatively complex movements of a person's body. For example, US 2007/0008156A1 describes a pressure-sensitive, piezoelectric sensor that is disposed in a zigzag manner along the side surfaces of a mattress. However, the sensor is merely used to detect patient contact with the side of the mattress (to avoid the inadvertent trapping of limbs or digits when adjusting a panel of an adjustable bed with a side rail or fence), and is not used (and indeed, cannot be used) to localize various, specific movements of a person on a mattress. As another example, US 2014/0371635A1 describes the placement of a single motion sensor on or under the side of a person's mattress, at a position above where the person rests his or her head. Once again, however, the sensor is not used, and cannot be used, to localize various, specific movements of a person on a mattress.

Thus, although many techniques have been used or proposed to monitor patient motion, each such technique is associated with significant drawbacks.

BRIEF DESCRIPTION OF THE DRAWINGS

FIG. 10 depicts an exemplary algorithm for tracking a patient's "still time" based on determined motion categories.

DETAILED DESCRIPTION

Figure 1:
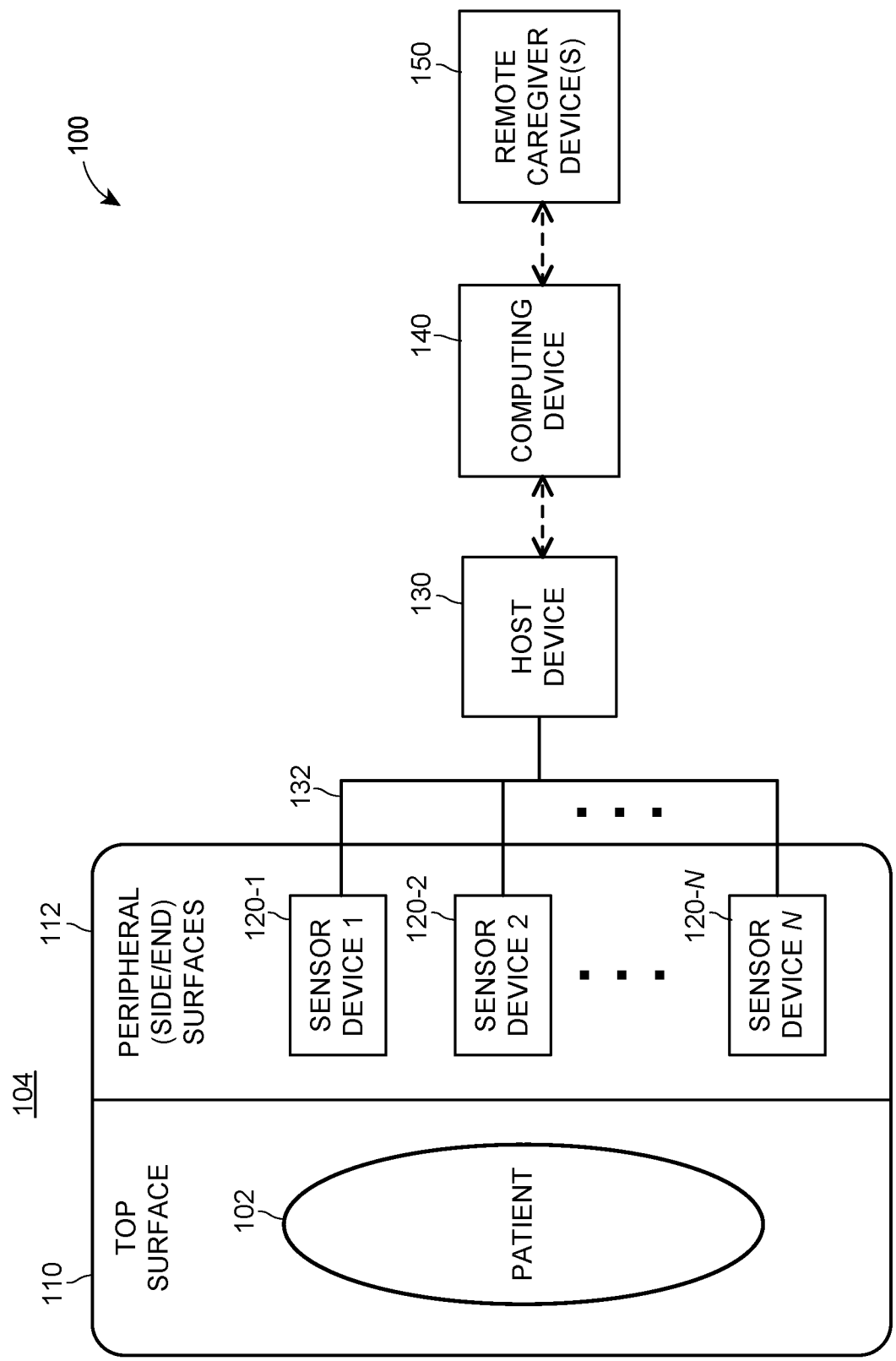
FIG. 1 is a block diagram of an exemplary monitoring system for alerting caregivers to certain situations in which a patient on a mattress may require assistance.

For a person to move while in bed, he or she must push down on one part of the bed mattress with one body part in order to develop enough propulsive force to accelerate another body part in accordance with the desired movement. As an example, in order for a supine individual to lift one leg from the bed, he or she must first push the hip and buttock of the leg that is to be lifted down into the mattress. The downward force exerted by the hip and buttock causes the mattress to be depressed under that part of the body. Moreover, it is a physical fact that, when something pushes downward on a mattress, the sides of the mattress will bulge outwards, due to a phenomenon known as the Poisson effect. Similarly, in order to roll the torso to one side, one must push the lower extremities down into the bed, thereby developing a large enough friction force against the mattress to generate the necessary counter torque. The Poisson effect ensures that the downward force on the mattress will result in a lateral movement of points on the side wall/surface of the mattress.

Embodiments described herein leverage the Poisson effect to provide a real-time monitoring system, which can detect one or more types of clinically important patient motions while the patient is in bed (or in a chair), without necessarily including any components that must come into contact with the patient. As used herein, the terms "patient" and "person" are used interchangeably, and neither term requires that the individual be admitted as a patient, or treated by a professional caregiver, unless the context of its usage so indicates. Moreover, the terms "motion" and "movement" may refer to patient motions, or to the absence of any (or any particular) patient motion, unless the context of its usage indicates one versus the other. In one embodiment, for example, the monitoring system can detect the following clinically important patient motions: (1) lack of motion for an excessive time (e.g., to prevent decubitus ulcers in critically ill patients); (2) motions indicative of a near-term bed egress (e.g., to enable caregivers to prevent physically unstable patients from falling, and/or detaching wires or tubes); and/or (3) repetitive physical motions that may be indicative of seizure activity (e.g., to provide caregivers an early warning of seizures for patients with epilepsy).

In some embodiments, the various motions are detected by positioning multiple, discrete, motion-sensing devices on each of one or both lateral sides of the bed mattress. The sensor devices may be mounted to the mattress side(s) using hook-and-loop patches, or may be integrated on or within the sides of the mattress during manufacture, for example.

The sensed motions of the mattress side(s) correspond to location-specific downward pressures, forces, and/or displacements on the top surface of the mattress, due to the Poisson effect (i.e., the phenomenon in which downward forces on the mattress cause lateral movement/bulging of the mattress side walls/surfaces).

Each sensor device may be placed at an appropriate position along the length of the mattress side(s) to ensure that a number of basic patient movements can be identified and distinguished. For example, on one or both sides of the mattress, sensor devices may be positioned proximate to (and laterally of) the prone patient's shoulders (and/or head), hips, and heels. Other sensor positions, such as one or both ends of the bed (on the mattress peripheral wall), are also possible. The software may translate the various Poisson effect displacements to localized downward forces (or pressures, displacements, etc.) on the mattress, identify basic movement phases and/or categories based on the location and/or pattern of the downward forces, and then analyze those movement phases and/or categories to determine whether, for instance, the patient is attempting to exit the bed, or whether the patient has not moved sufficiently for a long time. Alternatively, the software may use the direct measurements (e.g., acceleration or displacement) from the sensors to identify the basic movement phases and/or categories, without translating the measurements to downward forces and/or locations. Other processing techniques may also be used, such as analyzing the spectral content of the sensor readings to detect repetitive motions that may be indicative of clonic seizure.

These and other aspects and embodiments, as summarized above and/or as described in further detail below, can provide significant advantages relative to prior art devices and techniques. For example, as compared to many other approaches described above, the real-time monitoring system may better distinguish specific patient movements, and therefore do a better job of identifying specific, clinically important movements without an undue number of "false positives." Further, the described aspects/embodiments may result in increased versatility of mattress/sheet materials and/or greater patient comfort (e.g., by avoiding the need for mattress materials that cause excessive moisture/friction, and/or avoiding the need for the patient to wear additional sensors/devices), greater freedom of movement for the patient (e.g., by avoiding the need to attach wires/leads to the patient), greater equipment durability (e.g., by avoiding the use of specially-designed mats/pads that may break down due to patient weight), reduced space requirements (e.g., as compared to x-ray machines and certain other devices), and/or safety improvements (e.g., by avoiding battery leakage/overheating and/or electromagnetic hazards associated with worn devices, and/or by avoiding electrical shock risks associated with urine or feces shorting electrical conductors). Other advantages may also attach to particular aspects/embodiments.

Referring now to FIG. 1, an exemplary monitoring system 100 is configured to alert caregivers to certain situations in which a patient 102 on a mattress 104 may require assistance. FIG. 4 is a block diagram representation of the monitoring system 100, with mattress 104 being represented as a top surface 110 and peripheral surfaces 112. Top surface 110 represents the surface of the mattress 104 on which patient 102 lies (or possibly sits, etc.), while peripheral surfaces 112 collectively represent the vertical sides or walls of mattress 104 that connect the top surface 110 to the bottom surface (not shown) of mattress 104. For example, the peripheral surfaces 112 may consist of two longer, lateral sides of mattress 104 and two shorter ends of mattress 104. In some embodiments, mattress 104 rests on a bed frame (e.g., a frame of a hospital bed with side rails, etc.).

As used herein, unless the context of its usage dictates a more specific meaning, the term "mattress" may refer to a bed mattress, a pad, a cushion, or any other type of deformable material(s) that can support a person. In some embodiments, for example, mattress 104 represents one or more cushions of a chair, such as a standard chair or a wheelchair. In one such embodiment, mattress 104 may include a seam, or thinner portion, that allows mattress 104 to easily hinge, thereby providing both a seat cushion and a back cushion. Alternatively, mattress 104 may consist of two or more separate cushions (e.g., unattached seat and back cushions). For ease of explanation, however, the majority of the description that follows (as well as the drawings) relates to an embodiment in which mattress 104 is a bed mattress. It is to be understood that the operating principles of a bed mattress embodiment may be extended to a chair mattress/cushion embodiment. For example, references below to "downward" forces on mattress 104 would, in the context of a chair embodiment, be in the downward direction for the seat cushion, but in a backwards/posterior direction for the back cushion. Similarly, references below to a "top" surface of mattress 104 would, in the context of a chair embodiment, be a top surface for the seat cushion, but a front/anterior surface for the back cushion.

The mattress 104 and its surfaces 110, 112, and any coverings thereupon (e.g., sheets), may be constructed in any suitable manner, and of any suitable material(s) that is/are deformable (e.g., urethane foam, latex foam, an aqueous material in a surrounding plastic sleeve, or some hybrid of these). In some embodiments, mattress 104 is a foam mattress covered with a water-impermeable mattress cover. For reasons that will become clear in the description that follows, the materials and the design of mattress 104 must be such that at least some of peripheral surfaces 112 are not overly isolated, in a mechanical sense, from downward forces exerted on top surface 110. In some embodiments, an exterior of top surface 110, and/or any coverings thereupon, is/are made entirely of materials that are known to be beneficial for use in close proximity to the skin, such as cotton or polyester.

Figure 2:
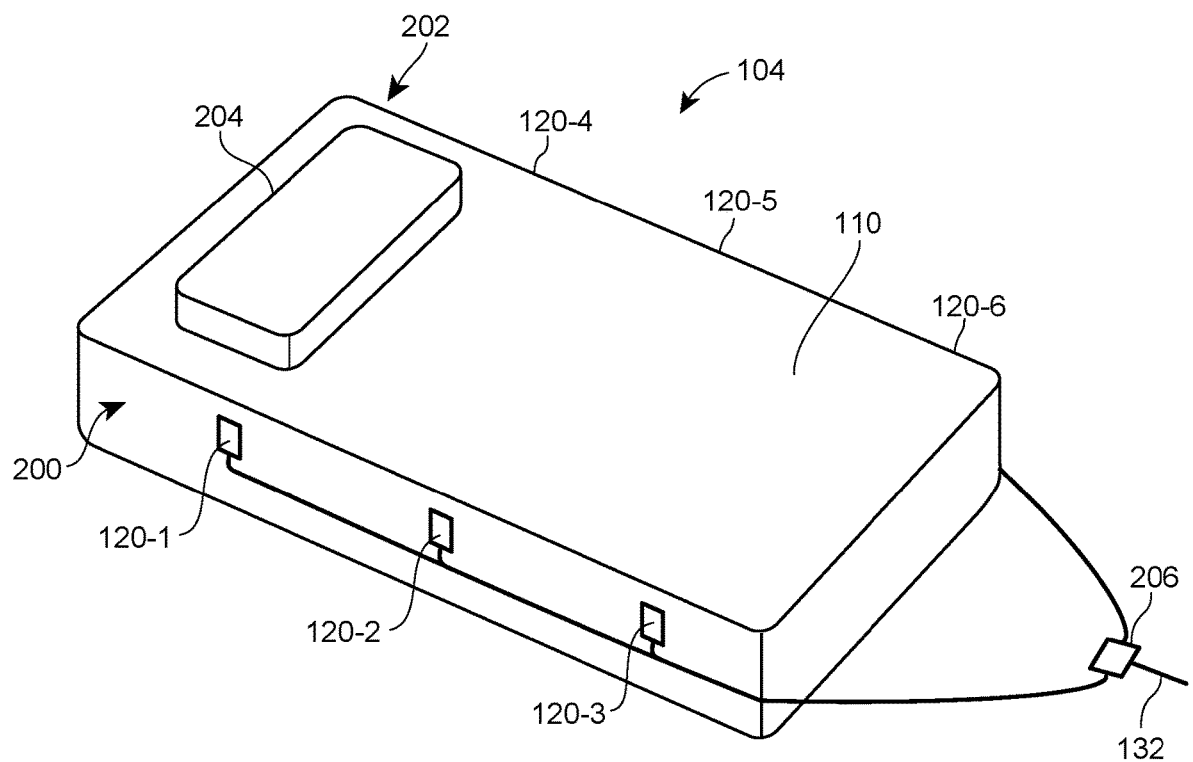
FIG. 2 depicts an exemplary mattress that may be used in the monitoring system of FIG. 1.

Positioned at a number of locations along one or more of peripheral surfaces 112 are N sensor devices 120, where N may be any integer greater than one (e.g., two, three, six, etc.), depending on the embodiment. In some embodiments, at least two (e.g., three) of sensor devices 120 are positioned at different points along one of the lateral/side surfaces of peripheral surfaces 112, with one of those sensor devices 120 being closer to the head end of mattress 104 and another being closer to the foot end of mattress 104. Moreover, in some embodiments, sensor devices 120 may be arranged along both lateral/side surfaces of peripheral surfaces 112, in a symmetric or asymmetric manner. For example, sensor devices 120 may include three sensor devices 120-1 through 120-3 on one side surface of mattress 104, and three additional sensor devices 120-4 through 120-6 directly opposite sensor devices 120-1 through 120-3, respectively, on the other side surface of mattress 104 (e.g., as shown in FIG. 2 and discussed below).

Each device of sensor devices 120 is able to sense/measure the motion (e.g., acceleration, velocity, displacement, and/or change in shape) of the particular portion of peripheral surfaces 112 on (or in) which that device is situated. In one embodiment, for example, each of sensor devices 120 includes an accelerometer. Alternatively, one, some, or all of sensor devices 120 may include a rate gyroscope, a displacement sensor, a magnetometer (sensing differences in the Earth's magnetic field based on location/displacement), and/or another suitable sensor type or types. In addition to the sensor (e.g., accelerometer) itself, each of sensor devices 120 may include a communication interface, and possibly other on-board processing, contained in a device enclosure. An example embodiment of one of sensor devices 120 is discussed below with reference to FIG. 3.

The system 100 monitors the outputs of sensor devices 120 to track the acceleration, velocity, displacement, and/or change in shape of one or more of peripheral surfaces 112. To this end, the outputs of sensor devices 120 may be provided to a host device 130 via a wired bus 132. Communications on bus 132 may adhere to an IIC protocol (also referred to as the "I2C" protocol) or an SPI protocol, for example. Alternatively, sensor devices 120 may include wireless (e.g., Bluetooth or WiFi) transmitters that provide the sensor output signals to host device 130.

In some embodiments, each of sensor devices 120 instead provides its output signals to a multiplexer (e.g., mounted on or resting near mattress 104, or directly coupled to host device 130, etc.), which is not shown in FIG. 1. Sensor devices 120 and the multiplexer may be connected by a multi-conductor wire, and the multiplexer and host device 130 may communicate over another wire using the IIC protocol, for example. An example embodiment including such a multiplexer is discussed below with reference to FIG. 2.

Host device 130 may include one or more processors (e.g., a microprocessor configured to execute instructions stored in a memory of host device 130, and/or hardware processors such as an application-specific integrated circuit (ASIC) or field-programmable gate array (FPGA)), one or more memory components for storing data (and possibly software instructions), and a communication interface configured to enable communications over bus 132. Generally, host device 130 may collect measurements/readings from sensor devices 120, perform various processing operations on the measurements, store historical measurements and/or motions in the local memory, and send notifications (e.g., alerts) and/or other messages to a computing device 140 to trigger user displays and/or alerts (e.g., for one or more caregivers). Host device 130 may include its processor(s), any memory, communication interface(s), etc., on one or more printed circuit boards contained in an enclosure, for example. Host device 130 may be powered via a wired cord or cable, or via a wireless charger. For example, host device 130 may be powered via a wireless charger that also serves as the power source for some or all of the other power-consuming portions of system 100.

Host device 130 may communicate with computing device 140 via a wireless or wired communication link that, once established, allows data to flow bi-directionally. Host device 130 and computing device 140 each include a communication interface that allows the respective device to communicate using the appropriate protocol (e.g., Bluetooth, WiFi, etc.). In some embodiments, computing device 140 is a personal computer, such as a portable computing device (e.g., a tablet device or a smartphone), or a desktop computer at a nursing station, and includes a microprocessor configured to execute software instructions stored in a memory of computing device 140 (e.g., to execute an application that enables computing device 140 to generate and present certain displays, and possibly perform other operations, as discussed below). In alternative embodiments, computing device 140 implements the functionality of host device 130, in which case host device 130 is not included in system 100, and sensor devices 120 (or a multiplexer in communication with sensor devices 120 as discussed above) communicate directly with computing device 140. In some embodiments, computing device 140 is located near mattress 104, such that a nurse walking by the patient's room can quickly look in the direction of the display of computing device 140, and determine whether any immediate action is necessary.

Generally, and as discussed in more detail below, computing device 140 generates and displays notifications (e.g., alerts) on a local display (e.g., monitor), and/or forwards notifications to one or more remote electronic caregiver devices 150. Computing device 140 may communicate with remote device(s) 150 via any suitable wireless communication link or links (e.g., cellular networks, the Internet, etc.), for example. Remote device(s) 150 may include any suitable electronic devices with audio and/or visual output capability, such as pagers, smartphones, and/or tablets, a nursing station computer, and/or a remote-controlled light or audio alarm at a nursing station, for example.

FIG. 2 depicts one example embodiment for mattress 104 of FIG. 1, with a specific, exemplary arrangement of sensor devices 120. In this example, three sensor devices 120-1 through 120-3 are positioned along a first lateral/side surface 200 of mattress 104 (i.e., one of the two longer, lateral surfaces of peripheral surfaces 112). While not visible in the perspective drawing of FIG. 2, in this embodiment, three additional sensor devices 120-4 through 120-6 are disposed on the opposite lateral/side surface 202 of mattress 104 (i.e., the other of the two longer, lateral surfaces of peripheral surfaces 112), with each one of sensor devices 120-4 through 120-6 being directly opposite a respective one of sensor devices 120-1 through 120-3 (relative to a central, longitudinal axis of mattress 104). A pillow 204 is shown in FIG. 2 merely to distinguish the head and foot ends of top surface 110.

In the depicted embodiment, each of sensor devices 120-1 through 120-6 is coupled by a conductive, shielded wire to a multiplexer 206, which is in turn coupled to host device 130 (not shown in FIG. 2) via wired bus 132, as discussed above. In some embodiments, host device 130 powers sensor devices 120-1 through 120-6 via the depicted wires/cables (e.g., by providing power that host device 130 itself receives via an external power cord and electrical outlet). Any cables may be physically routed in a manner so as to avoid tangles and interference with movements of the patient and any caregivers. Host device 130 may read sensor data/signals from multiplexor 206, e.g., by switching sequentially between the readings/signals of each of the different sensor devices 120. As noted above, in alternative embodiments, each of sensor devices 120-1 through 120-6 may instead communicate directly with host device 130 or computing device 140, and/or may communicate via a wireless communication link.

In the embodiment of FIG. 2, when patient 102 is on his or her back in a standard lying position, sensor devices 120-1 and 120-4 are positioned laterally (from a top-down view) of the patient's head or shoulders, sensor devices 120-2 and 120-5 are positioned laterally of the patient's hips, and sensor devices 120-3 and 120-6 are positioned laterally of the patient's feet. These positions may be advantageous because those body parts can be the most susceptible to skin breakdown and decubitus ulcers.

Each of sensor devices 120-1 through 120-6 may be affixed to the respective side surface (200 or 202) of mattress 104 using any suitable connector. To provide for easy retrofitting of an existing mattress, for example, each of sensor devices 120-1 through 120-6 may include a patch (e.g., connected to an enclosure of the sensor device 120 by adhesive) with a "hook" surface that is configured to mate to a "loop" surface on a patch located on mattress 104 (e.g., connected to mattress 104 by adhesive), or a "loop" surface that is configured to mate to a "hook" surface on a patch located on mattress 104. Alternatively, sensor devices 120-1 through 120-6 may be affixed to a pre-existing mattress 104 by other means, or may be integrated within the side walls of mattress 104 during manufacture of mattress 104. As another example, an elastic band may be fitted around all of peripheral surfaces 112 (inside of any mattress covering), with the sensor devices 120-1 through 120-6 being sandwiched between the band and the peripheral surfaces 112 such that the housing of the sensor devices 120-1 through 120-6 are compressed firmly against respective locations along the peripheral surfaces 112. This approach may provide better contact between sensor devices 120-1 through 120-6 and mattress 104 (e.g., if a mattress cover does not fit well onto mattress 104), and also better protects sensor devices 120-1 through 120-6 from bodily fluids or other matter. It is understood that any sensor or sensor device that is referred to herein as being positioned, placed, located, or mounted "on a mattress" (or on a particular surface of a mattress, etc.) may in actuality be mounted on a covering of the mattress (e.g., a fitted sheet), or some other component that is fitted or affixed to the mattress (e.g., if sensor devices 120 are attached to a single elastic band that extends around all of peripheral surfaces 112 as described above, or to multiple elastic bands that each extend around portions of top surface 110, side surfaces 200, 202, and the bottom surface of mattress 104).

Figure 3:
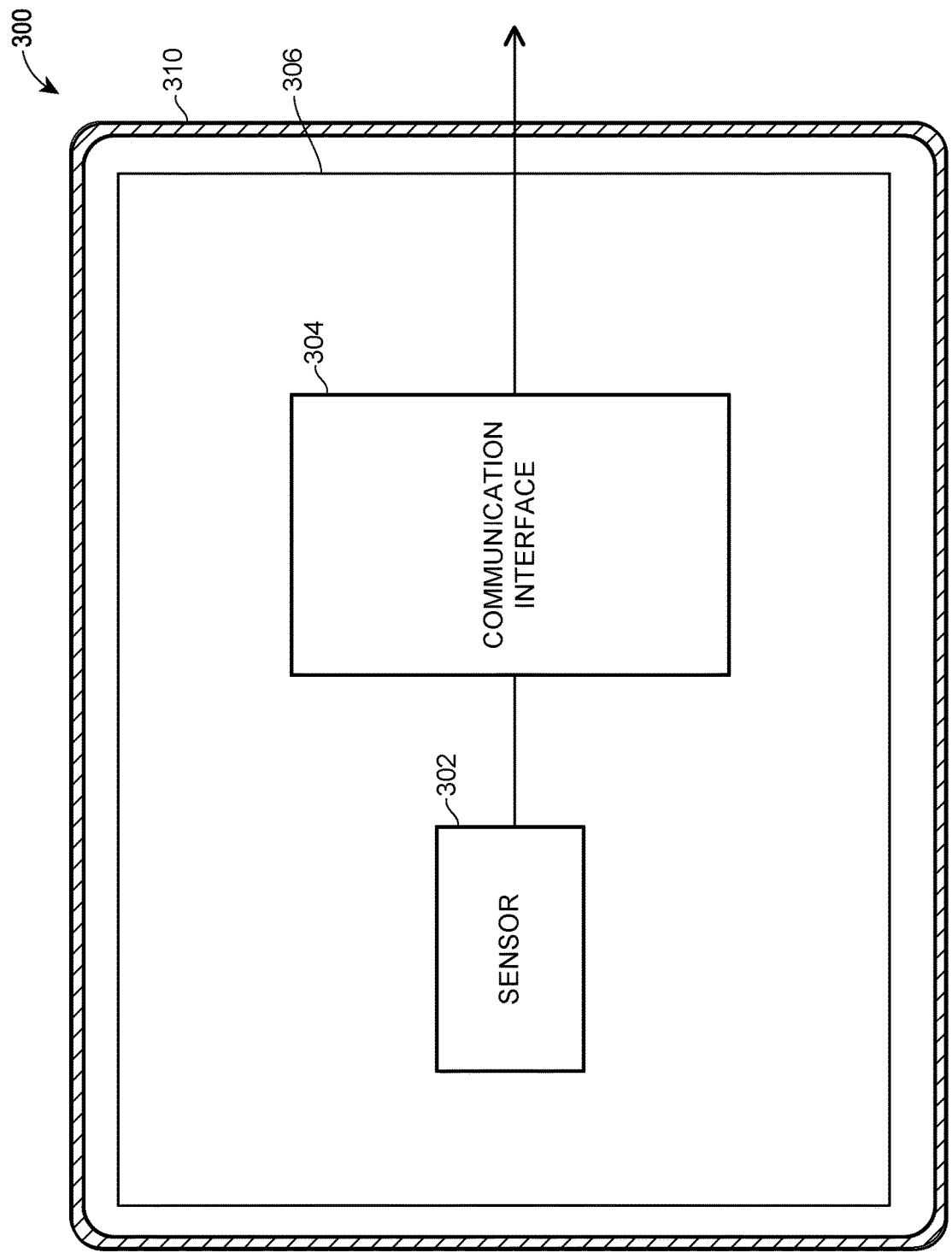
FIG. 3 is a diagram of an exemplary sensor device that may be used in the monitoring system of FIG. 1.

FIG. 3 depicts (partially in block diagram form) an exemplary sensor device 300 that may be used as any one or more of the sensor devices 120-1 through 120-N in FIG. 1 (e.g., as each of sensor devices 120-1 through 120-6 in FIG. 2). Sensor device 300 includes a sensor 302 which, as discussed above, may be an accelerometer or other type of sensor that is configured to detect motion (e.g., by sensing acceleration, velocity, displacement, and/or change in shape). Moreover, in some embodiments, sensor device 300 is capable of sensing motion in three dimensions (e.g., acceleration, velocity, and/or displacement components along each of three orthogonal axes). In one embodiment, for example, sensor 302 is an LIS3DH (MEMS digital output motion sensor) triple-axis accelerometer manufactured by STMicroelectronics.

Sensor 302 is electrically coupled to a communication interface 304, which enables communications with host device 130, either directly or via multiplexer 206 or another suitable intermediary component/device. Sensor 302 and communication interface 304 may be mounted on a printed circuit board 306, for example, with the board 306 (or multiple printed circuit boards) being contained within an enclosure 310. Enclosure 310 may be made of PVC, polyurethane, and/or any other suitable material(s). In embodiments where sensor device 300 communicates via a wired connection (e.g., with multiplexer 206), a conductive, shielded wire may extend from printed circuit board 306, out through a hole in enclosure 310.

While not shown in FIGS. 1 and 2, in some embodiments, monitoring system 100 may include one or more additional sensors in other locations. For example, system 100 may include an infrared device, a sonar device, a camera, and/or a microphone, any of which may be mounted to a pole, a bed frame element (e.g., rail, headboard, etc.), or another suitable location, and oriented so as to sense motions of the patient on mattress 104 (e.g., using image or audio processing techniques). These additional one or more sensors may couple to host device 130 via a wired or wireless communication link. In embodiments where any additional sensors are communicatively coupled via wires, cables between those sensors and host device 130 may provide a communication path and also power the additional sensors.

Operation of monitoring system 100 will now be described with reference to FIGS. 1 through 3, for the exemplary sensor arrangement shown in FIG. 2. In some embodiments, prior to use with a patient, each of sensor devices 120-1 through 120-6 must first be affixed to mattress 104 (directly, or by attaching to a fitted sheet on mattress 104, etc.). As noted above, for example, this may require that a nurse or other person attach one half of a hook-and-loop patch assembly to mattress 104, in each desired sensor location (e.g., after removing a non-stick backing from a patch to expose the adhesive), and then attach one of sensor devices 120-1 through 120-6 at each patch location (e.g., by pushing a hook or loop patch affixed to each of sensor devices 120-1 through 120-6 onto the loop or hook patch that is now affixed, by adhesive, to mattress 104). In embodiments where sensor devices 120-1 through 120-6 are manually attached to side surfaces 200, 202, the person doing so can advantageously adjust their placement according to the height of patient 102 while patient 102 is lying on mattress 104. Alternatively, the person may place sensor devices 120-1 through 120-6 according to anthropometric tables of the average height of the shoulder, buttocks, and heels above the ground for a standing person (adult or child), and by assuming that the buttocks of each patient will be approximately centered on mattress 104. In one embodiment, sensor devices 120-1 and 120-4 are mounted on side surfaces 200, 202 lateral of and below the shoulder area, sensor devices 120-2 and 120-5 are mounted on side surfaces 200, 202 lateral of and below the buttocks area, and sensor devices 120-3 and 120-6 are mounted on side surfaces 200, 202 lateral of and below the heel area (e.g., each with a particular placement tolerance, such as +/−10% of the height of the patient).

Figure 4A:
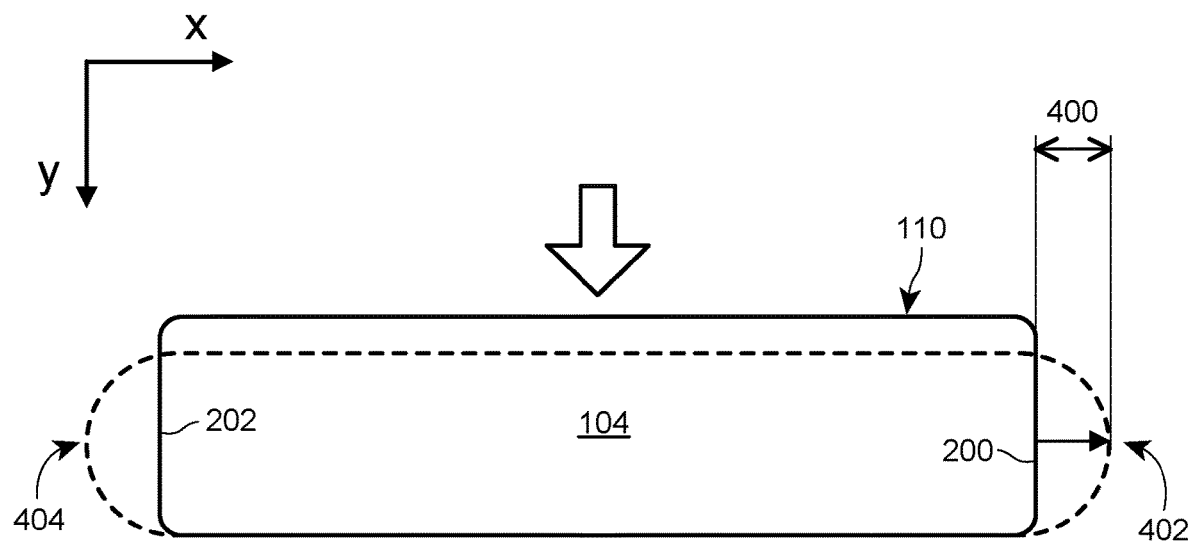
FIGS. 4A and 4B illustrate the Poisson effect, and potential non-uniform mattress characteristics, respectively.
Figure 9:
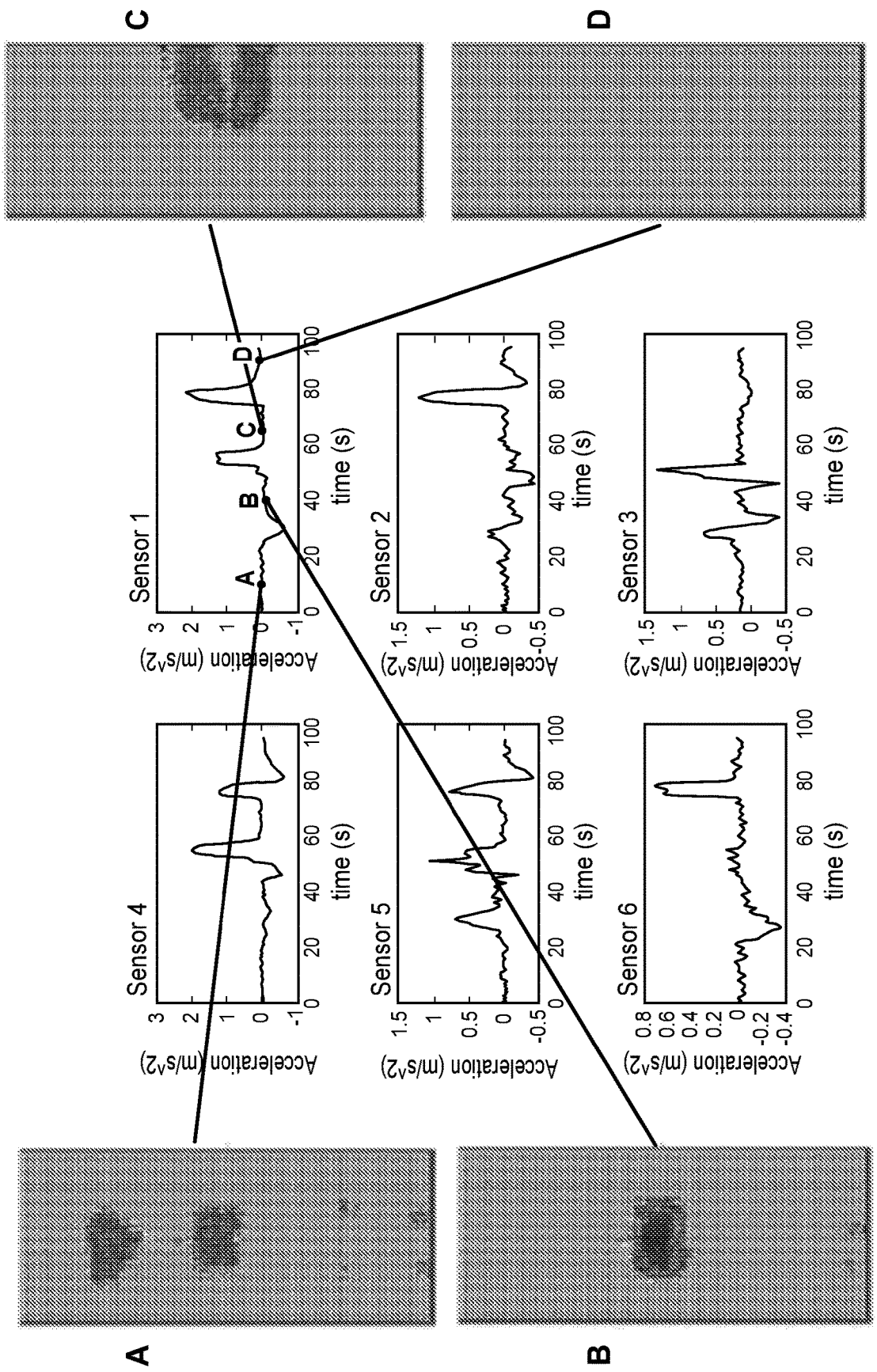
FIG. 9 depicts exemplary outputs that sensor devices may generate when a person exits a bed.

When a body segment of patient 102 exerts a downward force on various locations on top surface 110, the areas of side surface 200 and/or side surface 202 that are lateral of those locations become displaced (i.e., bulge) outwards due to the Poisson effect. This phenomenon is illustrated in a relatively simplistic manner in FIG. 4A, which shows a cross-sectional view of mattress 104 from the perspective of someone at the head end of mattress 104. As seen in FIG. 4A, a downward, axial force (here corresponding to the y-direction) on top surface 110 of mattress 104 induces a certain amount of lateral expansion, displacing side surfaces 200 and 202 in opposing transverse/lateral directions (here corresponding to the positive x-direction for side surface 200, and the negative x-direction for side surface 202). In this particular example, where the downward force is along the midline of mattress 104, both side surface 200 and side surface 202 are displaced by a distance 400. Of course, asymmetries in mattress 104 may cause surfaces 200, 202 to be displaced by different amounts. Generally, if the downward force is applied closer to side surface 200 than side surface 202, side surface 200 is displaced by a greater amount than side surface 202. Similarly, if the downward force is applied closer to side surface 202 than side surface 200, side surface 202 is displaced by a greater amount than side surface 200. In practice, of course, the body of patient 102 will cause downward force to be applied over a greater area (i.e., not just at a single point or along a single line) and, in many cases, will cause downward force to be applied simultaneously in multiple, non-contiguous areas along the width and/or length of mattress 104 (e.g., as shown in FIG. 9 and discussed below).

In some embodiments, each of sensor devices 120-1 through 120-6 is located along the midline of the side surface (200 or 202) on which it is positioned (i.e., in FIG. 4A, at a position approximately halfway between top surface 110 and the bottom surface of mattress 104, as indicated by arrows 402 and 404), in order to experience the largest possible acceleration, velocity, displacement, and/or change in shape when a downward force is applied on top surface 110. In other embodiments, each of sensor devices 120-1 through 120-6 is located at a different location to achieve this effect, such as about one inch below the outer edge of top surface 110 (e.g., inside of a water-impermeable mattress cover).

Figure 4B:
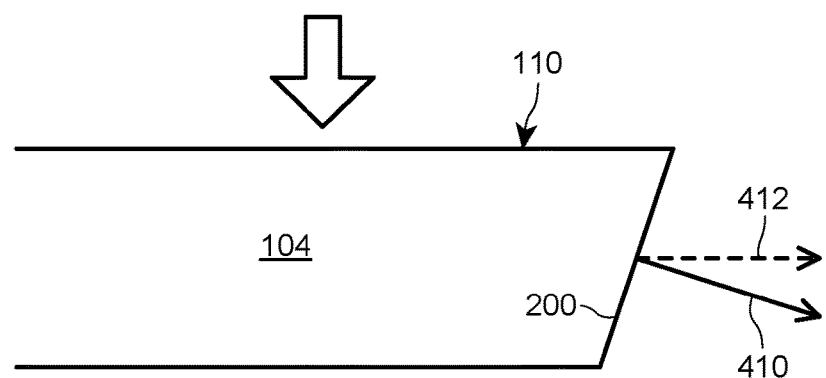

In some cases, mattress 104 may not respond to downward forces in the idealized manner shown in FIG. 4A. As seen in FIG. 4B, for example, mattress 104 may have a slightly tilted side surface 200 (and/or 202), which may result from construction tolerances, or from extended use of mattress 104 ("wear and tear"), etc. Alternatively, mattress 104 may exhibit such a tilt only when a shear load is applied to top surface 110.

As indicated by the arrows in FIG. 4B, when downward force is applied to top surface 110, such a tilt may cause the side surface 200 to protrude in a direction 410 rather than direction 412 (with direction 412 corresponding to displacement direction for an idealized version of mattress 104 as shown in FIG. 4A). Thus, there is a y-component to the displacement, velocity, and acceleration, as well as an x-component. In some embodiments and/or scenarios, there may even be slight displacements in the z-direction (i.e., orthogonal to the x- and y-axes) when downward force is applied to top surface 110. To account for these orthogonal components of displacement, velocity, and/or acceleration, as noted above, each of sensor devices 120-1 through 120-6 (or at least some of sensor devices 120) may be configured to sense motion in or along multiple (two or three) dimensions/axes.

Returning now to the operation of system 100, after sensor devices 120-1 through 120-6 are positioned appropriately on surfaces 200, 202 of mattress 104 (as shown in FIG. 2), sensor devices 120-1 through 120-6 are initialized and calibrated by an automated process, a manual process, or some combination thereof. Initialization may be a process that causes sensor devices 120-1 through 120-6 to establish a communication channel with host device 130, and to enter a "work" mode in which sensor 302 of each of sensor devices 120-1 through 120-6 generates sensor signals (i.e., measurements/readings), e.g., on a continuous or periodic basis. Calibration may be a process in which equation and/or algorithm parameters, and/or sensor settings, are adjusted based on measurements/samples that are collected under known conditions. If calibration fails for a given one of sensor devices 120-1 through 120-6, host device 130 may cause the corresponding sensor device to be disconnected, and may also send a message that causes an alert to be displayed to a caregiver (e.g., via a display of computing device 140, or via one or more of remote device(s) 150). Alerts may be provided as emails or text messages, in some embodiments (e.g., if one or more of remote device(s) 150 is/are a smartphone or personal computer with email and/or text message capability). In some embodiments, the calibration process involves a person (e.g., nurse) pushing down on specific locations of top surface 110 (e.g., on or near where the patient's shoulders, hips, and heels will be), while host device 130 identifies which of sensor devices 120-1 through 120-6 provide the greatest signal-to-noise ratio (SNR) for each push. Such a process may allow sensor devices 120-1 through 120-6 to be applied in any order at the shoulder/hip/heel locations, rather than requiring that each sensor device be applied at a specific location.

After (or during) sensor initialization and calibration, host device 130 may establish wireless communication with computing device 140. In some embodiments, a caregiver or other person must operate computing device 140 to search for host device 130 and initiate a request for a wireless connection (e.g., a Bluetooth request) with host device 130. Host device 130 may then reply with a consent or acknowledgment, at which point the connection is established.

Next, system 100 enters a continuous monitoring mode, e.g., in accordance with a programmed loop executing on host device 130 (e.g., as discussed below with reference to FIG. 6). In some embodiments the frequency and/or duration of measurement sampling and/or motion detection can be predefined by a developer or caregiver. In some embodiments, host device 130 checks whether sensor devices 120-1 through 120-6 are properly connected before each measurement, or on some other periodic basis. If a connection is broken, host device 130 may inform computing device 140, which may in turn generate a local audio and/or visual alert, and/or cause one or more of remote device(s) 150 to generate such an alert.

In scenarios where all connections are operating properly, sensor devices 120-1 through 120-6 continuously or periodically provide measurement signals to host device 130 (e.g., via multiplexer 206). Host device 130 may perform one or more processing operations on the measurements from sensor devices 120, and store the processed measurement data (and/or other data, such as indicators of patient movements corresponding to the measurement data) to a local memory. For example, in an embodiment where sensor 302 of each of sensor devices 120-1 through 120-6 is an accelerometer, host device 130 may process the accelerometer readings to remove the effects of acceleration due to gravity, in order to obtain linear absolute acceleration levels along one or more axes. As another example, in scenarios where mattress 104 exhibits some warping (e.g., as shown in FIG. 4B), host device 130 may process multi-axis components of the sensor readings to determine the vector of acceleration that should be used to calculate downward force on top surface 110.

In some embodiments, host device 130 may double integrate the processed (e.g., calibrated) acceleration values to obtain lateral/transverse displacement values for side surfaces 200, 202, and feed those displacement values into one or more motion categorization algorithms or models. Alternatively, host processor 130 may first map the lateral displacement values to downward forces (or pressures, weights, etc.) and their corresponding locations on top surface 110, in accordance with the Poisson effect, and feed those values into the motion categorization algorithm(s) or model(s). The ratio(s) and equation(s) for converting lateral displacement to downward forces/pressures/etc. depends on the material characteristics of mattress 104. The ratio(s)/equation(s) may be pre-calibrated/set by the developer based on those characteristics, for example. In still other embodiments, host device 130 may simply feed the raw or calibrated sensor measurements into the motion categorization algorithms or model(s). Some example algorithms for motion categorization/classification are discussed below with reference to FIGS. 7-10.

When an algorithm indicates that a particular alert condition is satisfied, host device 130 may send a corresponding message to computing device 140, to cause computing device to display an indication of the corresponding alert. In some embodiments and/or scenarios, computing device also communicates with remote device(s) 150 to cause each of those devices 150 to display an indication of the corresponding alert.

Figure 5A:
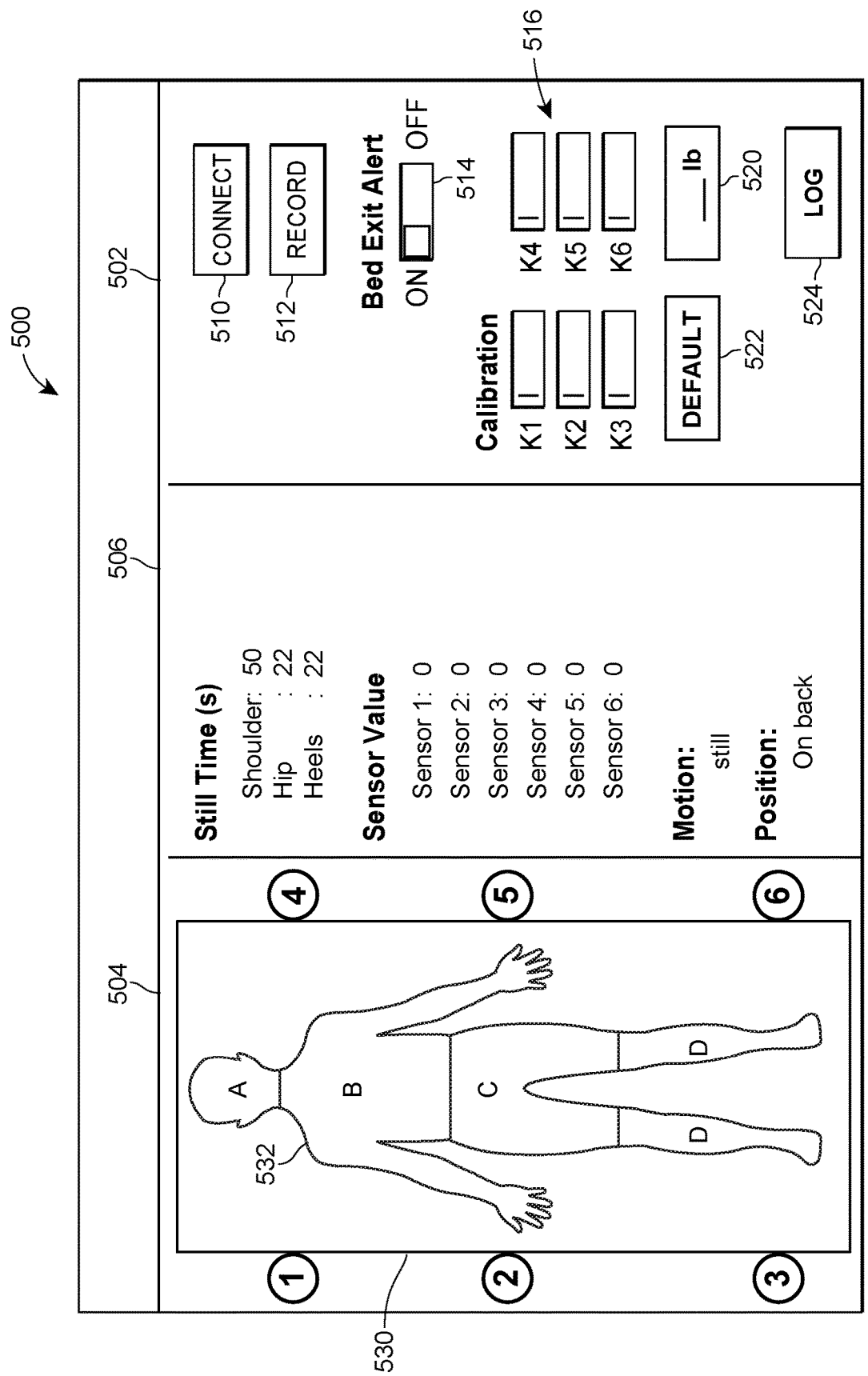
FIGS. 5A and 5B depict an exemplary graphical user interface (GUI) that the computing device of FIG. 1 may generate and display to a caregiver.
Figure 5B:
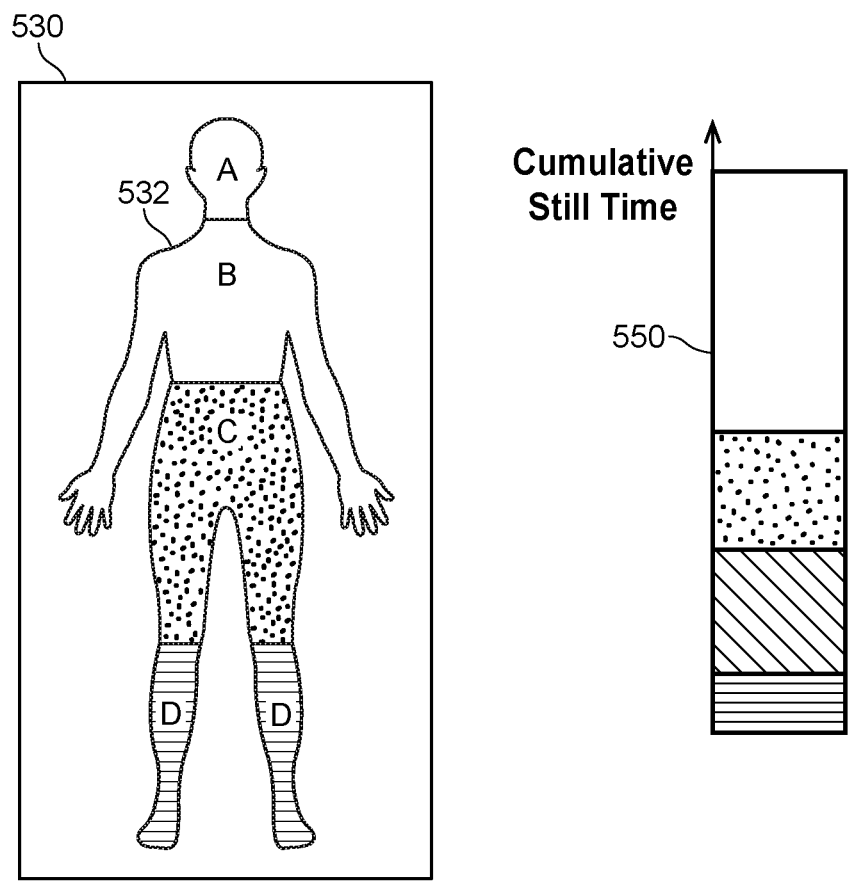

FIGS. 5A and 5B illustrate one exemplary graphical user interface (GUI) 500 that may be displayed to a user of computing device 140 (e.g., on a standard or touchscreen monitor of computing device 140), and/or may be displayed to a user of one or more of remote device(s) 150. The example GUI 500 includes a setup portion 502 that relates primarily to initialization and calibration, a patient visualization portion 504 that provides an easily-understood illustration of patient movement, and a measurement portion 506 that provides various sensor readings, as well as other information derived from those readings.

In setup portion 502, an interactive "CONNECT" control 510, when activated by the user (e.g., touched, or clicked upon using a mouse), initiates the establishment of the connection between host device 130 and computing device 140, as described above. More generally, the activation of control 510 may start operation of the entire system 100. Activation may cause control 510 to instead read "DISCONNECT," after which a second user activation may disconnect host device 130 from computing device 140 and/or stop operation of system 100.

An interactive "RECORD" control 512, when activated by the user, causes host device 130 to begin recording/storing data from sensor devices 120-1 through 120-6 for a predetermined time period, or until the user again activates control 512 (which may have changed to "STOP" after the initial activation). The historical measurements may be used for technical instruction or research purposes, for example, or to train a machine learning program of the sort discussed below.

A bed exit alert control 514 enables the user to activate or deactivate a motion categorization algorithm (or portion of a motion categorization algorithm) that detects when a patient is attempting to exit the bed, for an embodiment in which mattress 104 is a bed mattress. More generally, control 514 may disable an alert that is triggered when a patient is attempting to get off of mattress 104, regardless of whether mattress 104 is a bed mattress, a chair cushion (or cushions), etc. Control 514 may be convenient for caregivers, and may reduce "alarm fatigue" caused by too many triggers of the bed exit alarm.

Calibration parameters 516 may be manually defined/set values (i.e., with parameters 516 representing user controls), or may be values that are automatically determined by host device 130 when host device 130 implements the automatic calibration procedure. Alternatively, parameters 516 may be set in a partially automatic manner, e.g., if calibration involves manually pushing down on various areas of mattress 104 as discussed above. Calibration may be critical because body types/figures and body weights can vary dramatically, introducing uncertainties into the motion monitoring process.

An interactive weight field 520, when activated by the user (e.g., after system calibration), enables the user to enter a specific patient's weight, which is then used by host device 130 to update various coefficients or parameters of one or more motion categorization algorithms, and/or other coefficients/parameters. This may be viewed as an additional step of the calibration process, for example.

An interactive "DEFAULT" control 522, when activated by the user, causes some or all calibrated coefficients and/or parameters to return to their default state/setting, in which case the sensor data from sensor devices 120-1 through 120-6 may be presented in its raw form. An interactive "LOG" control 524, when activated by the user, causes sensor data to be output in log form (e.g., as a particular file type), e.g., for use in research or for personal care references.

In patient visualization portion 504, a graphic 530 represents mattress 104 (or a bed on which mattress 104 is placed, etc.), with numbered circles "1" through "6" representing locations of sensor devices 120-1 through 120-6, respectively. A patient graphic 532 is used to visualize patient status according to the extent (e.g., amount or force of movement, and/or frequency of movement, etc.) of motion recently and/or currently detected in each of four body regions: (A) head, (B) shoulders, torso, and possibly upper arms, (C) lower back/abdomen, hips, buttocks, upper thighs, and possibly lower arms/hands, and (D) mid and lower legs. Patient graphic 532 is discussed in further detail below, with reference to FIG. 5B.

In measurement portion 506, various readings/measurements provided by sensor devices 120-1 through 120-6 (possibly after calibration and/or other processing by host device 130) are displayed, possibly with other information that may be derived from those readings/measurements. In the example embodiment shown, measurement portion 506 shows the current sensor value from each of sensor devices 120-1 through 120-6. In addition, measurement portion 506 shows values that host device 130 determines based on the sensor values over time, including the "still time" since the last movement (or significant movement) of each of the shoulders, hips, and heels, a classification of the patient's overall motion (e.g., "still" or "moving" or "bed exit," etc.), and an indicator of the patient's currently estimated position (e.g., "on back" or "on right side" or "on stomach," etc.). In some embodiments, GUI 500 or another user interface enables an engineer or caregiver to predefine the number of motion and/or position categories, and/or the overall number and/or type of readings and related values displayed in measurement portion 506.

FIG. 5B depicts graphics 530 and 532 of patient visualization portion 504 of GUI 500, in one potential embodiment and scenario. As seen in the scale 550 on the right-hand side of FIG. 5B (which may or may not be displayed in GUI 500), different visual patterns may correspond to different cumulative still time ranges indicative of different patient statuses. For purposes of decubitus ulcers, for example, the top range on scale 550 (e.g., still time>120 minutes) may be indicative of an unhealthy status (e.g., insufficient patient movement), the next highest range (e.g., 120 minutes≥still time>60 minutes) may be indicative of moderate to high risk of decubitus ulcers in the respective body region, the next highest range (e.g., 60 minutes≥still time>30 minutes) may be indicative of a low to moderate risk of decubitus ulcers in the respective body region, and the lowest range (e.g., still time≤30 minutes) may be indicative of a healthy status in the respective body region.

Host device 130 or computing device 140 determines which pattern to apply in each body region of patient graphic 532 based on the readings/measurements (e.g., acceleration values) from one or more of sensor devices 120-1 through 120-6 (e.g., after the processing by host device 130). For example, the SNR indicated for region "C" may be a peak value from the pair of sensor devices 120-2 and 120-5 over a predetermined, recent time window, or an average of the peak values from sensor devices 120-2 and 120-5 over that time window, etc. The visualization may be used by a caregiver, in conjunction with the shown "still times," to assess an overall risk of decubitis ulcers. Alternatively, the visualization may account for both SNR and "still time" when showing a particular risk level.

In the scenario represented by FIG. 5B, the patient has very low risk of decubitus ulcers in the head and shoulder areas, a somewhat higher risk of decubitus ulcers in the hip/buttock area, and a still higher risk of decubitus ulcers in the lower leg and heel area. Thus, a caregiver observing GUI 500 would very likely want to ensure that at least the lower body regions of the patient are moved without delay.

It is understood that other embodiments may include more or fewer body regions in patient graphic 532, or may omit patient graphic 532, etc. For example, patient graphic 532 may include only three body regions, each corresponding to one of sensor device pairs 120-1/120-4, 120-2/120-5, and 120-3/120-6. In some embodiments, patient graphic 532 provides a continuous view rather than dividing graphic 532 into discrete body regions. Moreover, in some embodiments, different colors or other visual characteristics may be used instead of, or in addition to, the different patterns shown in FIG. 5B.

Figure 6:
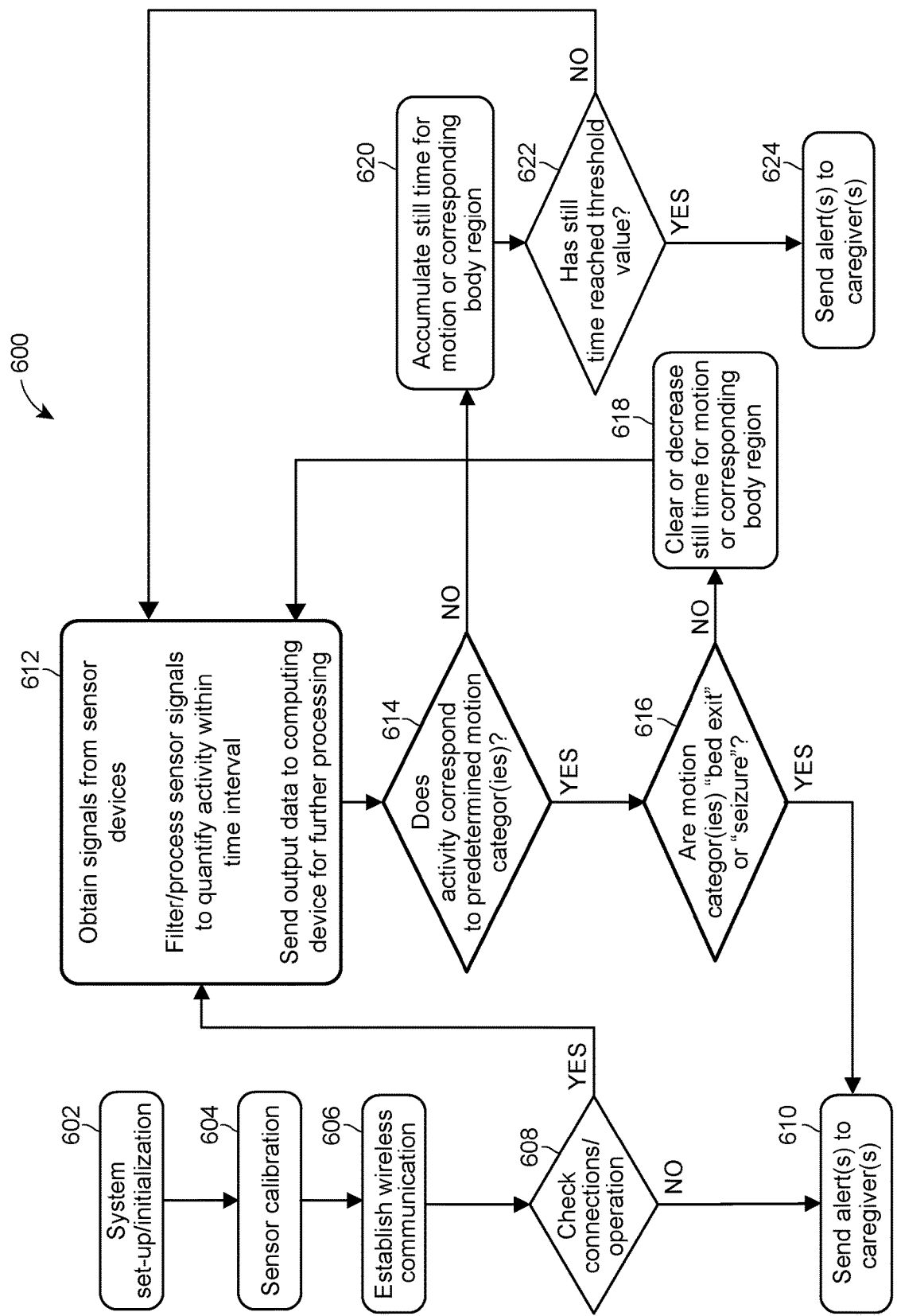
FIG. 6 is a flow diagram of an exemplary process that may be implemented by the monitoring system of FIG. 1.

FIG. 6 is a flow diagram of an exemplary process 600 that may be implemented by monitoring system 100 of FIG. 1. Process 600 may be implemented by host device 130 and/or computing device 140. In some embodiments, particular stages (e.g., calibration) may in part be implemented manually. Some or all of the stages shown in FIG. 6 may be implemented in the manner discussed above with respect to FIGS. 1 through 5, for example.

At stage 602, host device 130 (possibly with manual assistance) sets up and initializes system 100. Thereafter, at stage 604, host device 130 calibrates sensor devices 120. Either during or after system initialization and calibration, at stage 606, host device 130 and computing device 140 establish wireless communication.

Next, at stage 608, host device 130 checks whether sensor devices 120 are properly connected and/or functioning, and/or whether host device 130 has established communication with computing device 140. If all proper connections and/or operation cannot be confirmed, flow proceeds to stage 610, at which computing device 140 generates a local visual and/or audible alert, and/or sends one or more messages to remote device(s) 150 to cause device(s) 150 to generate a visual and/or audible alert. If proper connections and/or operation are confirmed, however, flow proceeds to stage 612.

A programmed loop, corresponding to a continuous monitoring mode of system 100, begins at stage 612. Alternatively, the loop may also encompass stage 608 (e.g., by checking connections/operation at regular intervals). At stage 612, host device 130 obtains signals/readings from sensor devices 120, filters and/or processes the sensor signals to quantify a level of activity within a given time interval (e.g., a time since a last round of sensor readings were obtained, or over a time window corresponding to multiple readings from each of sensor devices 120, etc.), and sends output data to computing device 140 for further processing. The time interval (and thus, frequency of detection), as well as the duration of monitoring, may be predefined by a developer or caregiver. In an alternative embodiment, all processing not related to alert generation occurs at host device 130, such that stage 612 does not include sending output data to computing device 140 (other than for possible display purposes).

At stage 614, computing device 140 (or host device 130) applies one or more algorithms to determine whether the sensor signals obtained and processed at stage 612 (in some embodiments, after twice integrating acceleration measurements to obtain displacements of side surfaces 200, 202) correspond to one or more predetermined motion categories. If so, flow proceeds to stage 616, where it is determined whether the motion categor(ies) include "bed exit" or "seizure." If so, flow proceeds to stage 610, in order to provide one or more alerts indicative of bed exit or seizure to one or more caregivers. If not, flow proceeds to stage 618, where a "still time" that host device 130 or computing device 140 is tracking/counting, corresponding to the motion categor(ies) determined at stage 614 and/or a related body region, is either cleared or decreased (e.g., reset to zero). After (or concurrent with) stage 618, flow returns to stage 612.

Returning to stage 614, if it is instead determined that the sensor signals do not correspond to a certain motion category or categories, flow proceeds to stage 620. At stage 620, the "still time" for the determined motion categor(ies) and/or a related body region accumulates (e.g., is incremented by one, or another suitable amount), after which flow proceeds to stage 622. At stage 622, host device 130 or computing device 140 determines whether the "still time" has reached a predetermined threshold value (e.g., 10,000 cycles of the programming loop, or 2 hours, etc.). If so, flow proceeds to stage 624. Stage 624 may be similar to stage 610, but with each alert specifically indicating a lack of motion, and/or risk of ulcers, etc. Alternatively, if the "still time" has not reached the threshold value, flow proceeds back to stage 612 for the next loop of the program.

Any suitable algorithm(s) may be used to determine whether specific sensor readings and/or combinations of sensor readings, at a single time instant and/or over multiple sensor sampling times, correspond to specific motion categories. The algorithm(s) may be developed through experiments, sophisticated logical statements, and/or machine learning, and validated through real-world experiments.

Figure 7:
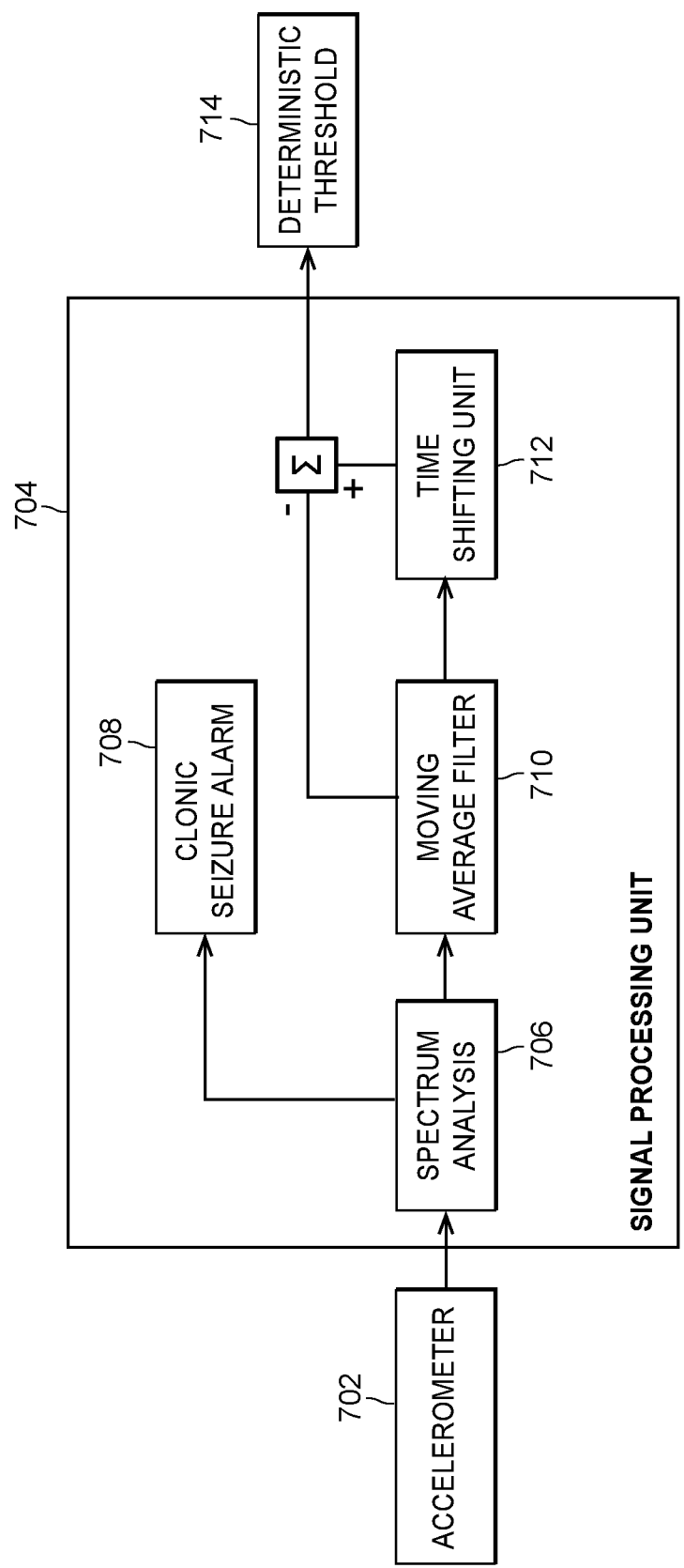
FIG. 7 depicts exemplary signal processing that the monitoring system of FIG. 1 may implement for a single sensor device.

As one example, FIG. 7 depicts exemplary signal processing 700 that a monitoring system (e.g., system 100) may implement for a single sensor device (e.g., each one of sensor devices 120). In FIG. 7, an accelerometer 702, which senses a mediolateral acceleration of a particular location on the side (or possibly head or foot end) of a mattress (e.g., mattress 104), may represent a sensor 302 in one of sensor devices 120. In other embodiments, as noted above, accelerometer 702 may instead be a different type of sensor that senses acceleration, velocity, displacement, and/or change in shape of a mattress side or end surface.

The acceleration values generated by accelerometer 702 (e.g., raw measurement values, or calibrated values) are fed into a signal processing unit 704. Signal processing unit 704 may be implemented by one or more processors of host device 130 or computing device 140, for example. Within signal processing unit 704, a spectrum analysis module 706 detects whether the acceleration values, over time, vary at an abnormal frequency. In some embodiments, for instance, spectrum analysis module 706 detects whether the acceleration values vary with a strong frequency component between 3 and 5 Hz, a range that is classically associated with clonic seizure. If the detected signal (e.g., signal energy) in that frequency range (or, in some embodiments, the detected signal above some minimum frequency, such as 3 Hz) is above a predetermined threshold level, a clonic seizure alarm routine 708 is triggered. For example, routine 708 may involve generating a seizure alert message and sending the message to computing device 140 to trigger an alarm at computing device 140 and/or remote device(s) 150.

The output of spectrum analysis module 706 (e.g., values representing signal energy versus frequency), or the acceleration values themselves, may be provided to a moving average filter 710, to filter out high frequency noise. The filtered signal then passes to a time shifting unit 712. The output of moving average filter 710 is subtracted from the output of time shifting unit 712 (or vice versa) to provide a signal indicating the difference in acceleration over time. The output is indicative of any loading or unloading occurring on the mattress, and in some embodiments may be applied to a deterministic threshold 714 to determine whether the sensor has detected a "significant" movement. In some embodiments, the comparison with deterministic threshold 714 also occurs within signal processing unit 704.

Figure 8:
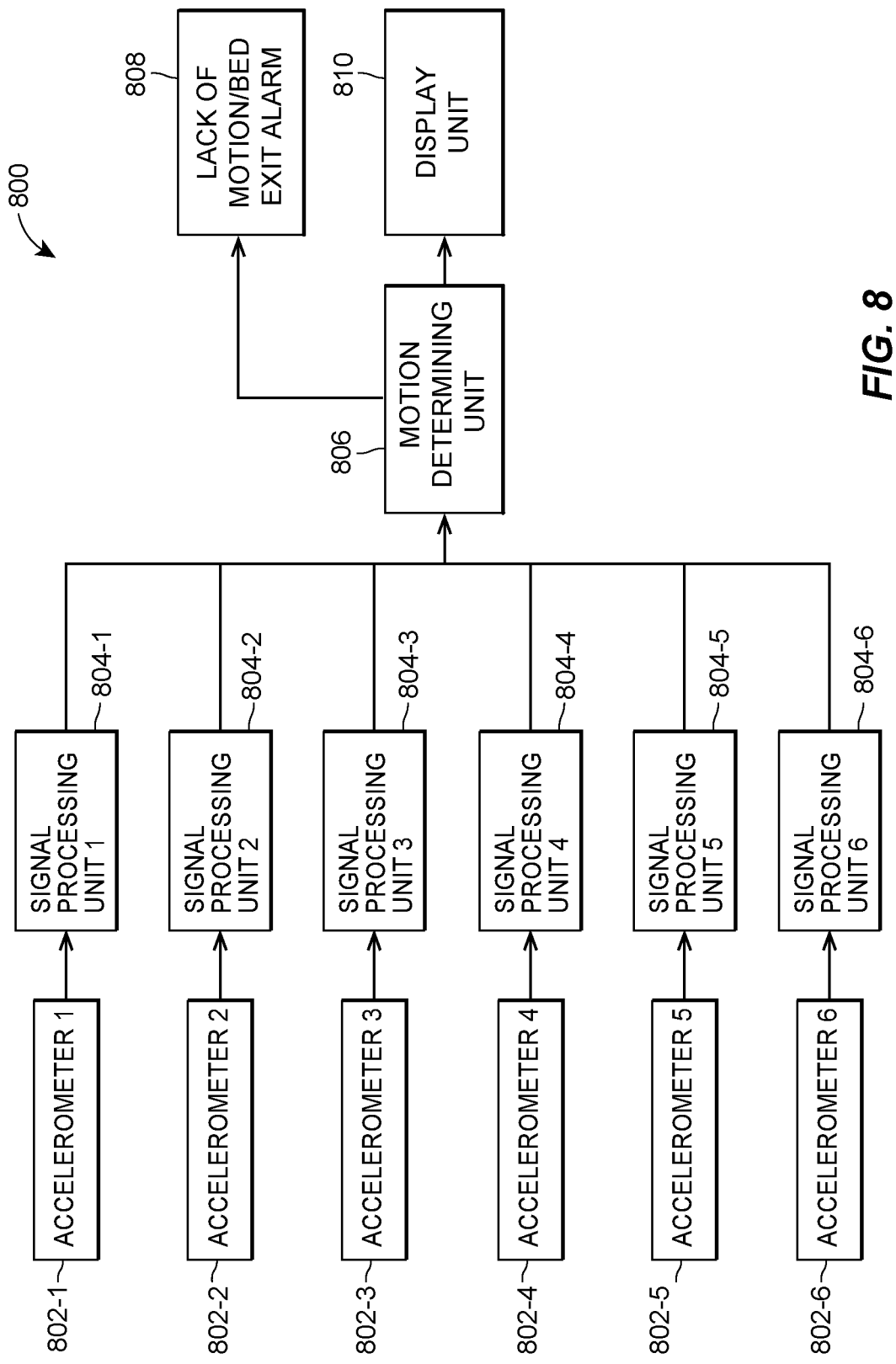
FIG. 8 depicts exemplary signal processing that the monitoring system of FIG. 1 may implement for a set of sensor devices.

FIG. 8 depicts exemplary signal processing 800 within a monitoring system that includes six sensor devices (e.g., system 100 with sensor devices 120-1 through 120-6). Each of accelerometers 802-1 through 802-6 may be identical to accelerometer 702, and each of signal processing units 804-1 through 804-6 may be identical to signal processing unit 704, for example. In some embodiments, two or more of accelerometers 802-1 through 802-6 is/are located on a side surface of the mattress (e.g., side surface 200 and/or 202), while one or more others is/are located on the head and/or foot end vertical surface. In other embodiments, all of accelerometers 802-1 through 802-6 are located on one or both side surfaces (e.g., as shown in FIG. 2). Apart from accelerometers 802-1 through 802-6, signal processing 800 may be implemented by one or more processors of host device 130 and/or computing device 140.

The signals output by each of signal processing units 804-1 through 804-6 (e.g., signals indicating comparisons with respective deterministic thresholds or, in some embodiments, the values of the difference signals) are provided to a motion determining unit 806, which classifies the set of motions from the signal processing units 804-1 through 804-6 into one or more pre-defined motion categories. If the motion determining unit 806 classifies the motions as "lack of motion" or "bed exit," an alarm routine 808 is triggered. For example, routine 808 may involve generating a lack of motion or bed exit alert message and sending the message to computing device 140 to trigger an alarm at computing device 140 and/or remote device(s) 150. Depending on the embodiment, different alarms (e.g., different messages) may be generated for bed exit and lack of motion, or the same alarm may be generated in both circumstances. In some embodiments, a display unit 810 of computing device 140 may show any suitable information (e.g., GUI 500 of FIG. 5) according to the requirements of caregivers.

In some embodiments, motion determining unit 806 executes a sensor fusion algorithm. For each of accelerometers (and/or other sensor types) 802-1 through 802-6, for example, the respective one of signal processing units 804-1 through 804-6 may classify detected movements as one of a number of self-defined "movement phases" within the local sensor area. Table 1 shows an exemplary relationship between sensor output signals and movement phases, with $x_i$ representing the signal output from the $i^{th}$ signal processing unit 804-$i$, with i being an integer between 1 and 6 (or between 1 and N for an arbitrary number of sensors), and with $\sigma_i$ representing the standard deviation of measurements from the $i^{th}$ sensor, which is calculated during the calibration phase 604:

TABLE 1

| Movement Phase | Sensor Output Signal |
| --- | --- |
| UNLOADING II | $x_i > 10\sigma_i$ |
| UNLOADING I | $10\sigma_i \geq x_i > 5\sigma_i$ |
| STATIONARY | $5\sigma_i \geq x_i \geq -5\sigma_i$ |
| LOADING I | $-5\sigma_i \geq x_i > -10\sigma_i$ |
| LOADING I | $x_i < -10\sigma_i$ |

The various movement phases may be determined by the respective signal processing unit 804, or by motion determining unit 806. Table 2, below, shows an exemplary relationship between the movement phases defined in Table 1 and various motion categories, and may represent the rules applied by motion determining unit 806 to determine motion categories:

TABLE 2

| Motion Category | Movement Phases Based on Sensor Outputs |
| --- | --- |
| Lying Supine | STATIONARY for all six sensors |
| Left Roll | LOADING I for sensor 3, 4 and UNLOADING I for sensor 1, 2 |
| Right Roll | LOADING I for sensor 1, 2 and UNLOADING I for sensor 4, 5 |
| Foot Lift | Sensor 3, 6 NOT in STATIONARY PHASE |
| Arm Lift | Sensor 1, 4 NOT in STATIONARY PHASE |
| Bed Exit | LOADING I or LOADING II for any sensor, followed by UNLOADING II for the same sensor |

In Table 2, "sensor 1" through "sensor 6" may correspond to sensor device 120-1 through sensor device 120-6 of FIG. 2, for example. The motion categories shown may be pre-defined according to the requirements of caregivers, with biomechanical analysis being used to define the motion categories for the patient lying in bed. In order to perform a bed exit, for example, the patient may need to execute a left roll or a right roll before sitting up on the edge of the mattress. These maneuvers will result in loading detected by at least one of the sensors. When the patient leaves the mattress, the mattress rebounds, resulting in a significant unloading behavior. Accordingly, the sensor output should be a loading phase followed by a large unloading phase.

Small movements, such as minor finger movement (e.g., scratching), will not contribute significantly to pressure application or relief, and thus do not in themselves generally cause the system to detect anything other than the "lying supine" movement phase. A roll can be detected by virtue of the fact that a shoulder press accompanies each roll, and would generally be located closer to one side of the mattress than the other (or at least, to one specific side relative to where the patient's weight was previously centered). Small, pure foot movements may be observed only by sensor devices lateral of the patient's feet (e.g., sensor devices 120-3 and 120-6), and combined hip/foot movements may be observed by both the hip and foot sensor devices (e.g., sensor devices 120-2, 120-3, 120-5, and 120-6). Notably, shoulder area sensor devices (e.g., sensor devices 120-1 and 120-4) may also observe small signal increases, because leg movement is typically associated with a downward shoulder push. An attempted bed exit will usually involve a reduction of weight on the heel and shoulder mattress regions (e.g., sensed by sensor devices 120-1, 120-3, 120-4, and 120-6), and an increase of weight in the hip region (e.g., sensed by sensor devices 120-2 and 120-5). This could be confirmed by a large signal increase in the hip and shoulder region on one side of the mattress (e.g., sensed by sensor devices 120-1 and 120-2, or by sensor devices 120-4 and 120-5). Clonic seizure may be detected by one or more sensors as large levels of movements (e.g., in a predetermined frequency range) over a long or short time period. In one embodiment, if the period is longer than 5 seconds, host device 130 or computing device 140 determines that the movement is indicative of clonic seizure.

If sensors are judiciously placed, the probability of error in deciding that a lack of motion interval has ended decreases exponentially as the number of sensors detecting acceleration above a predetermined threshold increases. Thus, the probability of erroneously indicating that a lack of motion interval has ended is greatly decreased by the presence of multiple sensors. In some embodiments, motion determining unit 806 executes an algorithm that explicitly accounts for this exponential relationship, e.g., by calculating a probability of error as an exponential function of how many of the plurality of sensor devices sensed a particular motion (and possibly comparing that error probability to some predetermined threshold level, etc.).

In embodiments where additional sensor types are included (e.g., a camera, microphone, infrared, or sonar device on a pole or bed frame element), motion determining unit 806 may also process and account for those additional sensor signals. Alternatively, signals from the other sensor types may be processed by an entirely separate computing device in order to provide a failsafe monitoring system.

In some embodiments, motion category classification (and possibly also movement phase identification/classification) is performed by a trained machine learning program. For example, deep learning techniques may be used, e.g., with a neural network being trained based on manually labeled motion categories or phases associated with different sets of sensor output data (i.e., with the raw or processed data from each sensor being used as an input/feature for the training process). In this manner, the neural network may be trained to classify motions based on sensor signal "signatures."

FIG. 9 depicts exemplary outputs 900 that the sensor devices may generate when a person exits a bed. In FIG. 9, phases A, B, C, and D represent pressure maps corresponding to four phases of bed egress. It is understood that these pressure maps do not represent data obtained by the system 100 (e.g., sensors 120), but rather are shown for illustrative purposes to indicate how different body movements during bed egress may correspond to different readings from sensor devices 120-1 through 120-6 (labeled in FIG. 9 as "Sensor 1" through "Sensor 6," respectively) using a pressure mat.

In phase A, a patient is lying supine on the mattress (e.g., mattress 104). Correspondingly, there is no signal indicating movement, in any sensor. In phase B, the patient is sitting up with his/her body weight concentrated on the buttocks area, resulting in a loading signal. In phase C, the patient moves to one side of the mattress, with legs hanging over the mattress edge. Due to the release of some body weight loading on the mattress, an unloading behavior is exhibited. Finally, in phase D, the patient leaves the bed entirely, resulting in significant unloading of the sensors at the side of the mattress on which the patient exited.

FIG. 10 depicts an exemplary algorithm 1000 for tracking a patient's "still time" based on determined motion categories. Algorithm 1000, which may be executed by one or more processors of host device 130 and/or computing device 140, may operate upon the motion classifications/categories output by motion determining unit 806 of FIG. 8, for example. In the example of FIG. 10, algorithm 1000 runs separate "still time" counters for the shoulder, hip, and heel regions of the body. Up and down arrows indicate that algorithm 1000 increments or decrements, respectively, the corresponding counter. Alternatively, a down arrow may indicate that algorithm 1000 resets the corresponding counter to zero. Each dash ("—") in FIG. 10 may correspond to no change, a reset of all counters, and/or some other action (e.g., a particular alarm being triggered), for example.

When the patient stays still, it is likely that his or her entire body weight is exerted on the mattress under several body parts, including the regions where bones lie close to the skin. Accordingly, algorithm 1000 increments all counters in that situation. Conversely, left and right rolls each may greatly reduce the lack of motion hazard in all three regions, and thus algorithm 1000 decrements or resets all three counters. Small foot movements would relieve the pressure under the heels, but not the shoulders and hips. Thus, algorithm 1000 decrements or resets the heel counter, but not the shoulder and hip counters. Large foot movement (usually combined with hip movement) is often a good indicator of the lower body weight being reduced on the mattress. Thus, algorithm 1000 decrements or resets the hip and heel counters, but not the shoulder counter. Attempted bed exit and clonic seizure are recognized as immediate danger behaviors, and therefore trigger alerts so that additional assistance may be provided, as discussed above.

Figure 11:
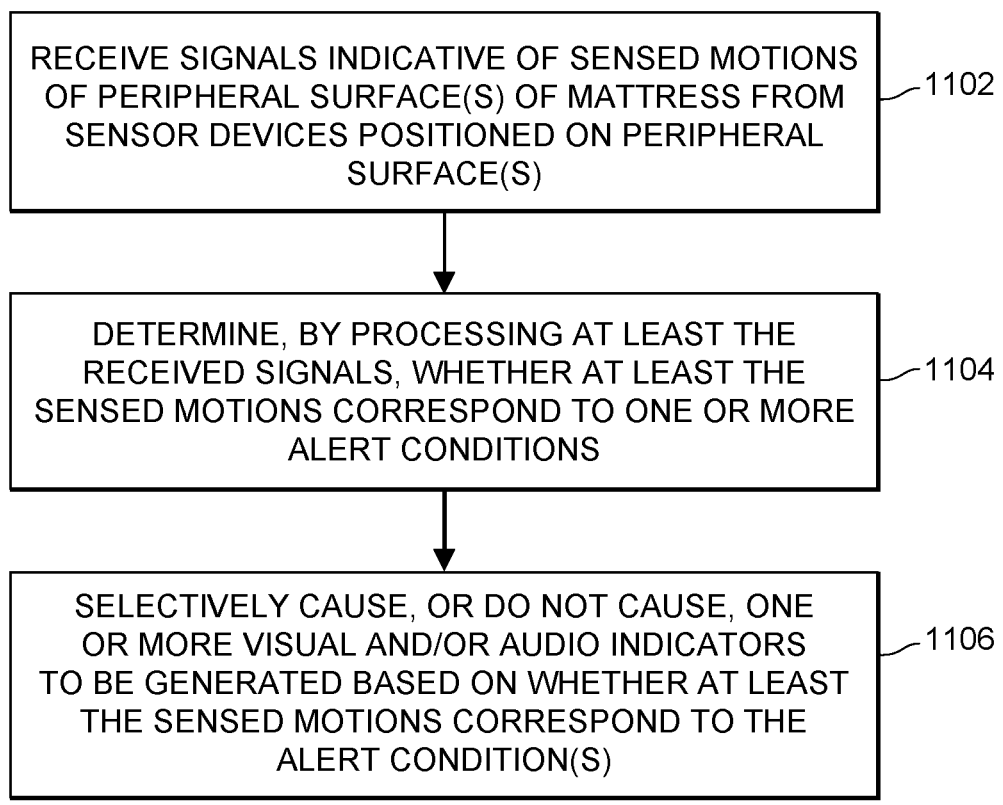
FIG. 11 is a flow diagram of an exemplary method for real-time monitoring of movements of a person on a mattress.

FIG. 11 is a flow diagram of an exemplary method 1100 for real-time monitoring of movements of a person on a mattress. Method 1100 may be implemented by a processing subsystem (e.g., one or more processors of host device 130 and/or computing device 140, when executing software instructions stored in a local memory of the respective device(s)).

At block 1102, signals indicative of sensed motion of one or more peripheral surfaces of a mattress are received (e.g., by host device 130) from sensor devices positioned on the one or more peripheral surfaces (e.g., from sensor devices 120-1 through 120-N). The peripheral surfaces connect the top and bottom surfaces of the mattress (e.g., surfaces generally parallel to the floor), and include first and second side surfaces as well as first and second end (e.g., head and foot end) surfaces.

The sensor devices include at least a first sensor device positioned on the first side surface and closer to the first end surface than to the second end surface (e.g., closer to the head end than the foot end of the mattress), and a second sensor device positioned on the first side surface and closer to the second end surface than to the first end surface (e.g., closer to the foot end than the head end). The first and second (and possibly additional) sensor devices may sense lateral motion (e.g., acceleration, velocity, displacement, change of shape, etc.) of the first side surface. In some embodiments, the sensor devices are arranged in accordance with FIG. 2. For example, the first sensor device may be positioned at a point along the first side surface that is less than one-third of a distance from the first end surface to the second end surface (e.g., at an expected head or shoulder position), the second sensor device may be positioned at a point along the first side surface that is more than two-thirds of the distance from the first end surface to the second end surface (e.g., at an expected heel position), and the third sensor device may be positioned at a point along the first side surface that is more than one-third and less than two-thirds of the distance from the first end surface to the second end surface (e.g., at an expected hip position).

At block 1104, it is determined (e.g., at host device 130 and/or computing device 140), by processing at least the signals received at block 1102, whether the sensed motions (and possibly also other factors) correspond to one or more alert conditions. Block 1104 may include any of the motion category (and possibly movement phase) classification algorithms or techniques discussed above (e.g., with reference to Tables 1 and 2, and FIGS. 6 through 8), and the alert condition(s) may include any of those discussed above (e.g., attempted bed egress, clonic seizure, and/or lack of movement), for example.

At block 1106, one or more visual and/or audio indicators are selectively caused, or not caused, to be generated, based on whether the sensed motions (and possibly also other factors) correspond to the one or more alert conditions. Block 1106 may be performed by host device 130, for example, and may include selectively sending, or not sending, an alert message from host device 130 to computing device 140 to cause computing device 140 to generate the indicator(s), and/or to trigger computing device 140 to send one or more additional messages to one or more remote electronic devices via a wireless network (e.g., to remote device(s) 150) to cause the remote device(s) to generate the indicator(s). Alternatively, block 1106 may be performed in whole or in part by computing device 140.

Figure 12:
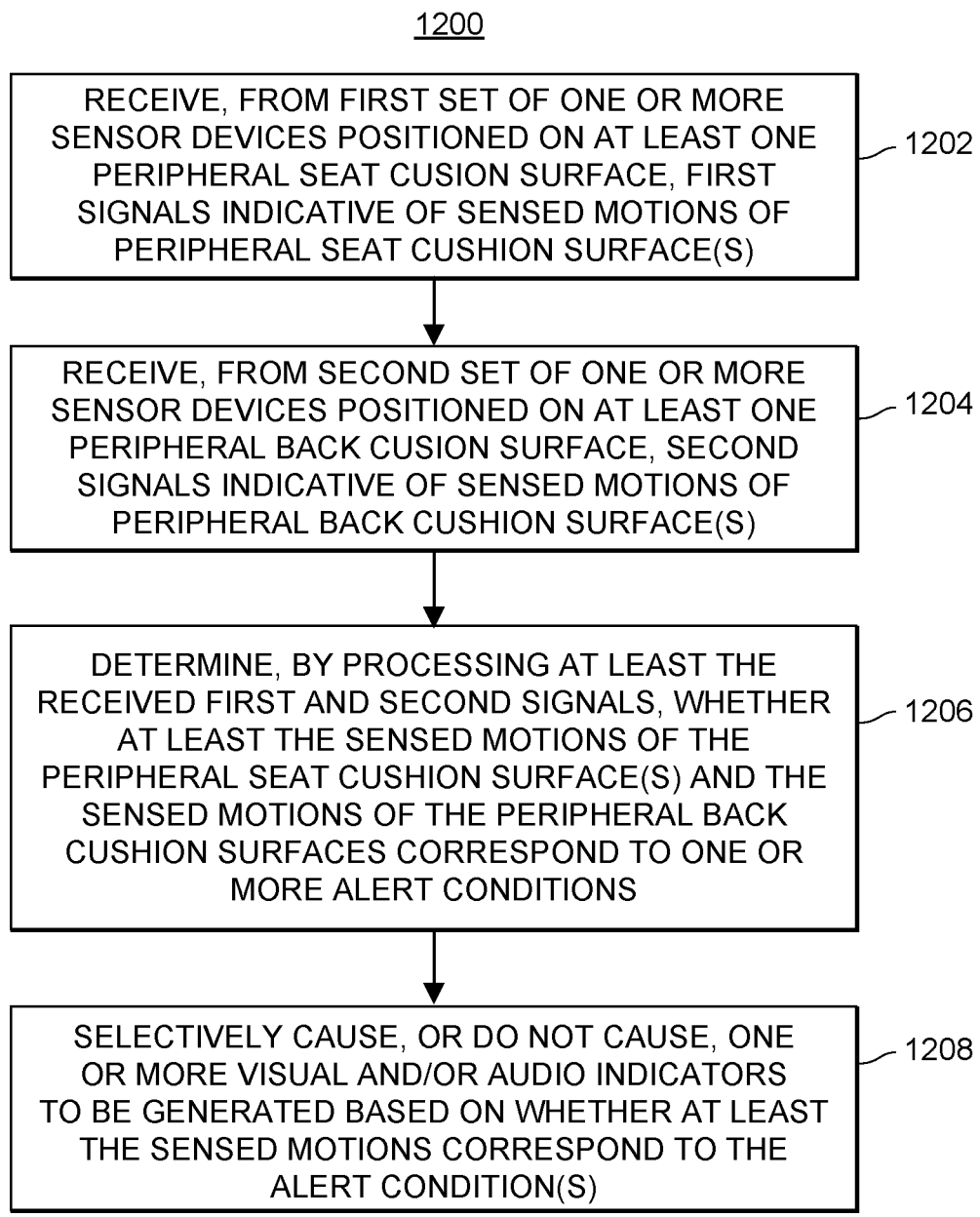
FIG. 12 is a flow diagram of an exemplary method for real-time monitoring of movements of a person in a chair.

FIG. 12 is a flow diagram of an exemplary method 1200 for real-time monitoring of movements of a person in a chair having a seat cushion and a back cushion. The seat cushion has top and bottom surfaces connected by one or more peripheral seat cushion surfaces, and the back cushion has anterior and posterior surfaces connected by one or more peripheral back cushion surfaces. The seat and back peripheral surfaces may vary in shape and number depending on the shape of the respective cushion (e.g., circular, rectangular, etc.). With reference to the discussion above, the seat and back cushions may collectively form mattress 104, for example, in an embodiment where mattress 104 can easily fold to fit to fit on a chair, or in an embodiment where mattress 104 includes two separate cushions. Method 1200 may be implemented by a processing subsystem (e.g., one or more processors of host device 130 and/or computing device 140, when executing software instructions stored in a local memory of the respective device(s)).

At block 1202, first signals are received from a first set of one or more sensor devices positioned on at least one of the peripheral seat cushion surfaces. The first signals are indicative of sensed motions of the peripheral seat cushion surface(s) on which the sensor devices of the first set are positioned. Each device of the first set of sensor devices may be one of sensor devices 120, for example.

At block 1204, second signals are received from a second set of one or more sensor devices positioned on at least one peripheral back cushion surface. The second signals are indicative of sensed motions of the peripheral back cushion surface(s) on which the sensor devices of the second set are positioned. Each device of the second set of sensor devices may be another one of sensor devices 120, for example.

At block 1206, it is determined, by processing at least the first and second signals received at blocks 1202 and 1204, whether the sensed motions (and possibly also other factors) correspond to the one or more alert conditions. Block 1206 may be similar to block 1104 of FIG. 11, for example, but with the alert conditions (and any classification of motion categories and/or movement phases) corresponding to a person sitting in a chair rather than a person in a bed. For example, the alert condition(s) may include "lack of motion" and/or "clonic seizure" alert conditions similar to the alert conditions described above for patients in bed, and may or may not include a "chair exit" alert condition (and/or a "slumped to side" or "slumped forward" alert condition, etc.).

At block 1208, one or more visual and/or audio indicators are selectively caused, or not caused, to be generated, based on whether the sensed motions (and possibly also other factors) correspond to the one or more alert conditions. Block 1208 may be similar to block 1106 of FIG. 11, for example.

We claim:

1. A system for real-time monitoring of movement of a person on a mattress, the mattress having top and bottom surfaces connected by peripheral surfaces, the peripheral surfaces including first and second side surfaces and first and second end surfaces, and the system comprising:
   a plurality of sensor devices positioned on one or more of the peripheral surfaces and configured to sense lateral accelerations of the one or more peripheral surfaces in directions orthogonal to the one or more peripheral surfaces, wherein the plurality of sensor devices includes at least (i) a first sensor device positioned on the first side surface and closer to the first end surface than to the second end surface and (ii) a second sensor device positioned on the first side surface and closer to the second end surface than to the first end surface; and
   a processing subsystem communicatively coupled to the plurality of sensor devices and configured to
      receive signals indicative of the sensed lateral accelerations of the one or more peripheral surfaces from the plurality of sensor devices,
      determine, by processing at least the received signals, whether at least the sensed lateral accelerations of the one or more peripheral surfaces correspond to one or more alert conditions, and
      selectively cause, or not cause, one or more visual and/or audio alert indicators to be generated based on whether at least the sensed lateral accelerations of the one or more peripheral surfaces correspond to the one or more alert conditions.

2. The system of claim 1, wherein:
   the plurality of sensor devices includes a third sensor device;
   the first sensor device is positioned at a point along the first side surface that is less than one-third of a distance from the first end surface to the second end surface;
   the second sensor device is positioned at a point along the first side surface that is more than two-thirds of the distance from the first end surface to the second end surface; and
   the third sensor device is positioned at a point along the first side surface that is more than one-third and less than two-thirds of the distance from the first end surface to the second end surface.

3. The system of claim 2, wherein:
   the first sensor device is positioned laterally of an expected head or shoulder position of the person on the top surface;
   the second sensor device is positioned laterally of an expected heel position of the person on the top surface; and
   the third sensor device is positioned laterally of an expected hip position of the person on the top surface.

4. The system of claim 1, wherein:
   the plurality of sensor devices includes (i) a third sensor device positioned on the second side surface and closer to the first end surface than to the second end surface, and (ii) a fourth sensor device positioned on the second side surface and closer to the second end surface than to the first end surface; and the third sensor device and the fourth sensor device are configured to sense lateral accelerations of the second side surface in a direction orthogonal to the second side surface.

5. The system of claim 1, wherein the plurality of sensor devices includes:

one or more sensor devices positioned on the first end surface and configured to sense lateral accelerations of the first end surface in a direction orthogonal to the first end surface.

6. The system of claim 1, wherein each of the plurality of sensor devices is configured to sense accelerations of a respective one of the peripheral surfaces in three orthogonal directions.

7. The system of claim 1, wherein:

the processing subsystem includes
 a host device communicatively coupled to the plurality of sensor devices, and
 a computing device communicatively coupled to the host device and to one or more remote electronic devices;

the host device is configured to (i) determine whether at least the sensed lateral accelerations of the one or more peripheral surfaces correspond to the one or more alert conditions, and (ii) selectively cause, or not cause, the one or more remote electronic devices to generate the one or more visual and/or audio alert indicators at least by selectively sending, or not sending, an alert message to the computing device.

8. The system of claim 1, wherein:

(a) the one or more alert conditions include a clonic seizure condition, and the processing subsystem determines whether at least the sensed lateral accelerations of the one or more peripheral surfaces correspond to the clonic seizure condition at least by analyzing frequency content of (i) the received signals, or (ii) metrics derived therefrom;

(b) the one or more alert conditions include an attempted bed egress condition, and the processing subsystem determines whether at least the sensed lateral accelerations of the one or more peripheral surfaces correspond to the bed egress condition at least by comparing (i) the received signals, or (ii) metrics derived therefrom, to respective threshold values; or (c) the one or more alert conditions include a lack of motion condition, and the processing subsystem determines whether at least the sensed lateral accelerations of the one or more peripheral surfaces correspond to the lack of motion condition at least by comparing (i) the received signals, or (ii) metrics derived therefrom, to respective threshold values.

9. The system of claim 1, wherein the processing subsystem is configured to determine whether at least the sensed lateral accelerations of the one or more peripheral surfaces correspond to the one or more alert conditions using a trained machine learning model.

10. The system of claim 1, comprising an infrared or sonar sensor device mounted to a pole or a bed frame element and configured to sense motions of the person on the mattress, wherein the processing subsystem is communicatively coupled to the infrared or sonar sensor device, and wherein the processing subsystem is configured to:

receive additional signals indicative of the sensed motions of the person from the infrared or sonar sensor device;

determine, by processing at least the received signals and the received additional signals, whether at least the sensed motions of the person and the sensed lateral accelerations of the one or more peripheral surfaces correspond to the one or more alert conditions; and selectively cause, or not cause, the one or more visual and/or audio alert indicators to be generated based on whether at least the sensed motion of the person and the sensed lateral accelerations of the one or more peripheral surfaces correspond to the one or more alert conditions.

11. The system of claim 1, wherein each of the plurality of sensor devices includes a respective housing to which is affixed either a hook patch, or a loop patch, of a hook-and-loop connector, and wherein the respective housings of the plurality of sensor devices are compressed against the one or more peripheral surfaces by an elastic band that surrounds the first and second side surfaces and the first and second end surfaces.

12. The system of claim 1, comprising the mattress, wherein each of the plurality of sensor devices is embedded within the mattress.

13. A method for real-time monitoring of movement of a person on a mattress having a top surface and a bottom surface connected by peripheral surfaces, the peripheral surfaces including first and second side surfaces and first and second end surfaces, and the method comprising:

receiving, by a processing subsystem, signals indicative of sensed lateral accelerations of one or more of the peripheral surfaces, in directions orthogonal to the one or more peripheral surfaces, from a plurality of sensor devices positioned on the one or more peripheral surfaces, the plurality of sensor devices including at least (i) a first sensor device positioned on the first side surface and closer to the first end surface than to the second end surface, and (ii) a second sensor device positioned on the first side surface and closer to the second end surface than to the first end surface;

determining, by the processing subsystem processing at least the received signals, whether at least the sensed lateral accelerations of the one or more peripheral surfaces correspond to one or more alert conditions; and selectively causing or not causing, by the processing subsystem, one or more visual and/or audio indicators to be generated based on whether at least the sensed lateral accelerations of the one or more peripheral surfaces correspond to the one or more alert conditions.

14. The method of claim 13, wherein:

the plurality of sensor devices includes a third sensor device; and while receiving the signals indicative of the sensed lateral accelerations of the one or more peripheral surfaces,
 the first sensor device is positioned at a point along the first side surface that is less than one-third of a distance from the first end surface to the second end surface,
 the second sensor device is positioned at a point along the first side surface that is more than two-thirds of the distance from the first end surface to the second end surface, and
 the third sensor device is positioned at a point along the first side surface that is more than one-third and less than two-thirds of the distance from the first end surface to the second end surface.

15. The method of claim 14, wherein, while receiving the signals indicative of the sensed lateral accelerations of the one or more peripheral surfaces:
- the first sensor device is positioned laterally of an expected head or shoulder position of the person on the top surface;
- the second sensor device is positioned laterally of an expected heel position of the person on the top surface; and
- the third sensor device is positioned laterally of an expected hip position of the person on the top surface.

16. The method of claim 13, comprising receiving, from each of the plurality of sensor devices, signals indicative of sensed accelerations of a respective one of the peripheral surfaces in three orthogonal directions.

17. The method of claim 13, wherein:
- receiving the signals indicative of the sensed lateral accelerations of the one or more peripheral surfaces includes receiving the signals at a host device of the processing subsystem;
- determining whether at least the sensed lateral accelerations of the one or more peripheral surfaces correspond to the one or more alert conditions is performed at the host device; and
- selectively causing, or not causing, the one or more visual and/or audio alert indicators to be generated includes selectively sending, or not sending, an alert message from the host device to a computing device of the processing subsystem.

18. The method of claim 13, wherein:
the one or more alert conditions include a clonic seizure condition; and
determining whether at least the sensed lateral accelerations of the one or more peripheral surfaces correspond to the clonic seizure condition at least by analyzing frequency content of (i) the received signals, or (ii) metrics derived therefrom,
and wherein
- the one or more alert conditions include an attempted bed egress condition, and determining whether at least the sensed lateral accelerations of the one or more peripheral surfaces correspond to the bed egress condition at least by comparing (i) the received signals, or (ii) metrics derived therefrom, to respective threshold values, or
- the one or more alert conditions include a lack of motion condition, and determining whether at least the sensed lateral accelerations of the one or more peripheral surfaces correspond to the lack of motion condition at least by comparing (i) the received signals, or (ii) metrics derived therefrom, to respective threshold values.

19. The method of claim 13, wherein determining whether at least the sensed lateral accelerations of the one or more peripheral surfaces correspond to the one or more alert conditions includes calculating a probability of error as an exponential function of how many of the plurality of sensor devices sensed acceleration.

20. The method of claim 13, wherein determining whether at least the sensed lateral accelerations of the one or more peripheral surfaces correspond to the one or more alert conditions includes using a trained machine learning model to determine whether at least the sensed lateral accelerations of the one or more peripheral surfaces correspond to the one or more alert conditions.

21. A system for real-time monitoring of movement of a person in a chair, the chair having a seat cushion and a back cushion, the seat cushion having top and bottom surfaces connected by one or more peripheral seat cushion surfaces, the back cushion having anterior and posterior surfaces connected by one or more peripheral back cushion surfaces, and the system comprising:
- a first set of one or more sensor devices positioned on at least one of the peripheral seat cushion surfaces and configured to sense lateral accelerations of the at least one of the peripheral seat cushion surfaces in directions orthogonal to the at least one of the peripheral seat cushion surfaces;
- a second set of one or more sensor devices positioned on at least one of the peripheral back cushion surfaces and configured to sense lateral accelerations of the at least one of the peripheral back cushion surfaces in directions orthogonal to the at least one of the peripheral seat cushion surfaces; and
- a processing subsystem communicatively coupled to the first and second sets of sensor devices, wherein the processing subsystem is configured to
  - receive first signals indicative of the sensed lateral accelerations of the at least one of the peripheral seat cushion surfaces from the first set of sensor devices,
  - receive second signals indicative of the sensed lateral accelerations of the at least one of the peripheral back cushion surfaces from the second set of sensor devices,
  - determine, by processing at least the received first signals and the received second signals, whether at least the sensed lateral accelerations of the at least one of the peripheral seat cushion surfaces and the sensed lateral accelerations of the at least one of the peripheral back cushion surfaces correspond to one or more alert conditions, and
  - selectively cause, or not cause, one or more visual and/or audio indicators to be generated based on whether at least the sensed lateral accelerations of the at least one of the peripheral seat cushion surfaces and the sensed lateral accelerations of the at least one of the peripheral back cushion surfaces correspond to the one or more alert conditions.

22. A method for real-time monitoring of movement of a person in a chair having a seat cushion and a back cushion, seat cushion having top and bottom surfaces connected by one or more peripheral seat cushion surfaces, the back cushion having anterior and posterior surfaces connected by one or more peripheral back cushion surfaces, and the method comprising:
- receiving, by a processing subsystem and from a first set of one or more sensor devices positioned on at least one of the peripheral seat cushion surfaces, first signals indicative of sensed lateral accelerations of the at least one of the peripheral seat cushion surfaces in directions orthogonal to the at least one of the peripheral seat cushion surfaces;
- receiving, by the processing subsystem and from a second set of one or more sensor devices positioned on at least one of the peripheral back cushion surfaces, second signals indicative of sensed lateral accelerations of the at least one of the peripheral back cushion surfaces in directions orthogonal to the at least one of the peripheral back cushion surfaces;
- determining, by the processing subsystem processing at least the received first signals and the received second signals, whether at least the sensed lateral accelerations of the at least one of the peripheral seat cushion surfaces and the sensed lateral accelerations of the at least one of the peripheral back cushion surfaces correspond to one or more alert conditions; and selectively causing or not causing, by the processing subsystem, one or more visual and/or audio indicators to be generated based on whether at least the sensed lateral accelerations of the at least one of the peripheral seat cushion surfaces and the sensed lateral accelerations of the at least one of the peripheral back cushion surfaces correspond to one or more alert conditions correspond to the one or more alert conditions.

* * * * *